(12) United States Patent
Zhang

(10) Patent No.: US 11,161,905 B2
(45) Date of Patent: Nov. 2, 2021

(54) RECOMBINANT ANTIBODIES TO PROGRAMMED DEATH 1 (PD-1) AND USES THEREOF

(71) Applicants: Ying Zhang, Hunan (CN); Xiangtan Tenghua Bioscience, Hunan (CN)

(72) Inventor: Ying Zhang, Hunan (CN)

(73) Assignee: XIANGTAN TENGHUA BIOSCIENCE, Xiangtan (CN)

(*) Notice: Subject to any disclaimer, the term of this patent is extended or adjusted under 35 U.S.C. 154(b) by 17 days.

(21) Appl. No.: 16/488,667

(22) PCT Filed: Mar. 4, 2017

(86) PCT No.: PCT/IB2017/051275
§ 371 (c)(1),
(2) Date: Aug. 26, 2019

(87) PCT Pub. No.: WO2018/162944
PCT Pub. Date: Sep. 13, 2018

(65) Prior Publication Data
US 2020/0062847 A1 Feb. 27, 2020

(51) Int. Cl.
*C07K 16/28* (2006.01)

(52) U.S. Cl.
CPC ...... *C07K 16/2818* (2013.01); *C07K 2317/24* (2013.01); *C07K 2317/33* (2013.01); *C07K 2317/76* (2013.01); *C07K 2317/92* (2013.01)

(58) Field of Classification Search
CPC ............ C07K 16/2818; C07K 2317/24; C07K 2317/33; C07K 2317/76; C07K 2317/92; A61P 35/00
See application file for complete search history.

(56) References Cited

U.S. PATENT DOCUMENTS 8,735,553 B1  5/2014 Li et al.

FOREIGN PATENT DOCUMENTS

| CN | 105175544 A | 12/2015 |
|---|---|---|
| CN | 105330740 A | 2/2016 |
| CN | 105683217 A | 6/2016 |
| WO | WO-2004/056875 A1 | 7/2004 |
| WO | WO-2013/173223 A1 | 11/2013 |
| WO | WO-2015/036394 A1 | 3/2015 |
| WO | WO-2015/112800 A1 | 7/2015 |
| WO | WO-2015/112900 A1 | 7/2015 |
| WO | WO-2016/020856 A2 | 2/2016 |
| WO | WO-2016/068801 A1 | 5/2016 |
| WO | WO-2016/077397 A2 | 5/2016 |
| WO | WO-2016/092419 A1 | 6/2016 |
| WO | WO-2016/106159 A1 | 6/2016 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Benson Jr., et al. "The PD-1/PD-L1 axis modulates the natural killer cell vers multiple myeloma effect: a therapeutic target for CT-01 1 , a novel monoclonal anti-PD-1 antibody", Blood. (2010), 116(13):2286-94.
Brahmer, et al. "Nivolumab vers docetaxel in advanced squamo-cell non-small-cell lung cancer", N Engl J Med. (2015), 373(2):123-35.
Garon EB, et al. "Pembrolizumab for the treatment of non-small-cell lung cancer", N Engl J Med. (2015), 372(21):2018-28 [94] NPL4.
Sharma, et al., "Immune checkpoint targeting in cancer therapy: toward combination strategies with curative potential", Cell. (2015), 161 (2):205-214.
Webster, "The immune checkpoint inhibitors: where are we now?", Nat Rev Drug Discov. (2014), 13(12):883-4.

* cited by examiner

*Primary Examiner* — Brad Duffy
*Assistant Examiner* — Cheom-Gil Cheong
(74) *Attorney, Agent, or Firm* — Ballard Spahr, LLP

(57) ABSTRACT

Provided are monoclonal antibody, particularly rabbit recombinant antibody, which specifically binds to human PD-1 with biological functions and super high affinity, and methods of use. In various embodiments, the antibodies are fully humanized antibodies that bind to human PD-1. Nucleic acid molecules encoding the antibodies and methods for expressing the antibodies are also provided. In some embodiments, the antibodies are useful for inhibiting or neutralizing PD-1 activity, thus providing a means of treating, preventing and/or diagnosing a disease or disorder such as cancer or a viral infection.

12 Claims, 12 Drawing Sheets
Specification includes a Sequence Listing.

a: Abs-r-923
c: Abs-r-924
e: Abs-r-925
h: Abs-r-926

Fig.3A

Rabbit Anti-PD-1 Abs-r-923 V$_H$

```
1   TGCCAGAGCGTGGAAGAAAGCGAAGGCGGCCTGGTGAAACCGGGCGCGAGCCTGACCCTG
     C  Q  S  V  E  E  S  E  G  G  L  V  K  P  G  A  S  L  T  L

61  AGCTGCACCGCGAGCGGCTTTACCCTGAGCAGCTATGCGATGCATTGGGTGCGCCAGGCG
     S  C  T  A  S  G  F  T  L  S  S  Y  A  M  H  W  V  R  Q  A
                    <------CDR1------>

121 CCGGGCAACGGCCTGGAATGGATTGGCTGGAGCAACGCGGGCAACGGCAACACCAAATAT
     P  G  N  G  L  E  W  I  G  W  S  N  A  G  N  G  N  T  K  Y
                                   <---------CDR2--------->

181 AGCCAGGAATTTCAGGGCCGCTTTACCATTACCCGCAACACCAGCCTGAGCACCGTGACC
     S  Q  E  F  Q  G  R  F  T  I  T  R  N  T  S  L  S  T  V  T

241 CTGGAAATGACCAGCCTGACCGCGGCGGATACCGCGACCTATTTTTGCGCGCGCTATTGG
     L  E  M  T  S  L  T  A  A  D  T  A  T  Y  F  C  A  R  Y  W
                                                         <----

301 TATTTTGATCTGTGGGGCCCGGGCACCCTGGTGACCGTGAGCAGC
     Y  F  D  L  W  G  P  G  T  L  V  T  V  S  S
     ------>
      CDR3
```

Fig.3B

Rabbit Anti-PD-1 Abs-r-923 V$_K$

```
1   GAACTGGTGCTGACCCAGACCCCGAGCAGCGTGAGCGCGGCGGTGGGCGGCACCGTGACC
     E  L  V  L  T  Q  T  P  S  S  V  S  A  A  V  G  G  T  V  T

61  ACAATTAACTGCCAGGCGAGCCAGAGCGGCAGCAGCTTTGTGGCGTGGTATCAGCAGAAA
     T  I  N  C  Q  A  S  Q  S  G  S  S  F  V  A  W  Y  Q  Q  K
                          <--------CDR1-------->

121 CCGGGCCAGCCGCCGAAACTGCTGATTTATGCGAACAACAAACGCGAAACCGGCGTGCCG
     P  G  Q  P  P  K  L  L  I  Y  A  N  N  K  R  E  T  G  V  P
                                <-----CDR2----->

181 AGCCGCTTTAGCGGCAGCGGCAGCGGCACCGATTTTACCCTGACCATTAGCAGCCTGGAA
     S  R  F  S  G  S  G  S  G  T  D  F  T  L  T  I  S  S  L  E

241 TGCGAAGATGCGGCGACCTATTATTGCGGCACCTATACCGATAGCCCGCCGACCTTTGGC
     C  E  D  A  A  T  Y  Y  C  G  T  Y  T  D  S  P  P  T  F  G
                               <----------CDR3---------->

201 GGCGGCACCAAAGTGGTGGTGAAAGGCGATCCG
     G  G  T  K  V  V  V  K  G  D  P
```

Fig.3C

Humanized Anti-PD-1 Abs-h-923 V$_H$

```
1   CAGGTGCAGCTGGTGCAGAGCGGCGCGGAAGTGAAAAAACCGGGCGCGAGCGTGAAAGTG
     Q   V   Q   L   V   Q   S   G   A   E   V   K   K   P   G   A   S   V   K   V

61  AGCTGCAAAGCGAGCGGCTATACCTTTACCAGCTATGCGATGCATTGGGTGCGCCAGGCG
     S   C   K   A   S   G   Y   T   F   T   S   Y   A   M   H   W   V   R   Q   A
                     ←--------- CDR1 ---------→

121 CCGGGCCAGCGCCTGGAATGGATGGGCTGGAGCAACGCGGGCAACGGCAACACCAAATAT
     P   G   Q   R   L   E   W   M   G   W   S   N   A   G   N   G   N   T   K   Y
                                         ←--------- CDR2 ---------→

181 AGCCAGGAATTTCAGGGCCGCGTGACCATTACCCGCGATACCAGCGCGAGCACCGCGTAT
     S   Q   E   F   Q   G   R   V   T   I   T   R   D   T   S   A   S   T   A   Y

241 ATGGAACTGAGCAGCCTGCGCAGCGAAGATATGGCGGTGTATTATTGCGCGCGCTATTGG
     M   E   L   S   S   L   R   S   E   D   M   A   V   Y   Y   C   A   R   Y   W
                                                                           ←-----

301 TATTTTGATCTGTGGGGCCGCGGCACCCTGGTGACCGTGAGCAGC
     Y   F   D   L   W   G   R   G   T   L   V   T   V   S   S
     ----- CDR3 ------→
```

Fig.3D

Humanized Anti-PD-1 Abs-h-923 V$_K$

```
1   GAGATCGCCCTGACCCAGAGCCCCGCTACACTGAGTCTGAGCCCTGGCGAGCGCGCAACA
     E   I   A   L   T   Q   S   P   A   T   L   S   L   S   P   G   E   R   A   T

61  CTGAGTTGCCGGGCCAGCCAGAGCGGCTCTAGCTTCGTGGCCTGGTATCAGCAGAAACCA
     L   S   C   R   A   S   Q   S   G   S   S   F   V   A   W   Y   Q   Q   K   P
                             ←----- CDR1 -----→

121 GGCCAAGCCCCCCGGCTCCTGATCTATGCCAACAACAAGAGAGAGACTGGCATCCCTGCC
     G   Q   A   P   R   L   L   I   Y   A   N   N   K   R   E   T   G   I   P   A
                                     ←--------- CDR2 ---------→

181 CGGTTCTCCGGATCAGGTTCCGGGACCGACTTTACCCTTACTATCTCCTCTCTGGAACCA
     R   F   S   G   S   G   S   G   T   D   F   T   L   T   I   S   S   L   E   P

241 GAAGACTTTGCTGTGTACTACTGCGGCACCTACACAGATTCACCCCCCACGTTCGGACAG
     E   D   F   A   V   Y   Y   C   G   T   Y   T   D   S   P   P   T   F   G   Q
                                     ←------------ CDR3 ------------→

301 GGGACCAAGGTGGAGATTAAGAGGACCGTG
     G   T   K   V   E   I   K   R   T   V
```

Fig.4A

Rabbit Anti-PD-1 Abs-r-924 $V_H$

```
1   CAGGAAAGCGTGAAAGAAAGCGGCGGCGGCCTGGTGAAACCGGGCGATACCCTGACCCTG
    Q   E   S   V   K   E   S   G   G   G   L   V   K   P   G   D   T   L   T   L

61  ACCTGCAAAGTGAGCGGCTTTAGCATTAGCAGCTATGGCATGCATTGGGTGCGCCAGGCG
    T   C   K   V   S   G   F   S   I   S   S   Y   G   M   H   W   V   R   Q   A
                        ◄────────CDR1────────►

121 CCGGGCAAAGGCCTGGAATGGATTGGCGTGATTAGCTATGATGGCAGCAACAAATATTAT
    P   G   K   G   L   E   W   I   G   V   I   S   Y   D   G   S   N   K   Y   Y
                                        ◄────────CDR2────────►

181 GCGGATAGCGTGAAAGGCCGCTTTACCATTAGCCGCAACACCAACCAGAACACCGTGACC
    A   D   S   V   K   G   R   F   T   I   S   R   N   T   N   Q   N   T   V   T

241 CTGAAAATGACCAGCCTGACCGCGGATGATACCGCGACCTATTTTTGCGCGCGCTATTAT
    L   K   M   T   S   L   T   A   D   D   T   A   T   Y   F   C   A   R   Y   Y
                                                                            ◄────

301 TATTATTATGGCATGGATGTGTGGGGCCAGGGCACCCTGGTGACCGTGAGCAGC
    Y   Y   Y   G   M   D   V   W   G   Q   G   T   L   V   T   V   S   S
    ────CDR3────►
```

Fig.4B

Rabbit Anti-PD-1 Abs-r-924 $V_K$

```
1   GAAATTGTGCTGACCCAGACCCCGAGCAGCGTGAGCGCGGCGGTGGGCAGCACCGTGACC
    E   I   V   L   T   Q   T   P   S   S   V   S   A   A   V   G   S   T   V   T

61  ACAATTAACTGCCGCGGCAGCCAGAGCCTGAGCAGCTATCTGGCGTGGTATCAGCAGAAA
    T   I   N   C   R   G   S   Q   S   L   S   S   Y   L   A   W   Y   Q   Q   K
                            ◄──────CDR1──────►

121 CCGGGCCAGCGCCCGAAACTGCTGATTTATGATGTGAGCAACCGCGCGACCGGCGTGCCG
    P   G   Q   R   P   K   L   L   I   Y   D   V   S   N   R   A   T   G   V   P
                                        ◄──────CDR2──────►

181 CGCCGCTTTAAAGGCAGCGGCAGCGGCACCCAGTTTACCCTGACCATTAGCGGCGTGCAG
    R   R   F   K   G   S   G   S   G   T   Q   F   T   L   T   I   S   G   V   Q

241 GCGGATGATGCGGCGACCTATTATTGCCAGCAGCGCACCAACTGGCCGCGCGCGTTTGGC
    A   D   D   A   A   T   Y   Y   C   Q   Q   R   T   N   W   P   R   A   F   G
                                        ◄────────CDR3────────►

301 GGCGGCACCAAAGTGGATGTGAAAGGCGATCCG
    G   G   T   K   V   D   V   K   G   D   P
```

Fig.4C

Humanized Anti-PD-1  Abs-h-924  V$_H$

```
1   CAGGTGCAGCTGGTGGAAAGCGGCGGCGGCGTGGTGCAGCCGGGCCGCAGCCTGCGCCTG
     Q  V  Q  L  V  E  S  G  G  G  V  V  Q  P  G  R  S  L  R  L

61  AGCTGCGCGGCGAGCGGCTTTACCTTTAGCAGCTATGGCATGCATTGGGTGCGCCAGGCG
     S  C  A  A  S  G  F  T  F  S  S  Y  G  M  H  W  V  R  Q  A
                     ◄═══════ CDR1 ═══════►

121 CCGGGCAAAGGCCTGGAATGGGTGGCGGTGATTAGCTATGATGGCAGCAACAAATATTAT
     P  G  K  G  L  E  W  V  A  V  I  S  Y  D  G  S  N  K  Y  Y
                                   ◄═══════════ CDR2

181 GCGGATAGCGTGAAAGGCCGCTTTACCATTAGCCGCGATAACAGCAAAAACACCCTGTAT
     A  D  S  V  K  G  R  F  T  I  S  R  D  N  S  K  N  T  L  Y
     ═══════►

241 CTGCAGATGAACAGCCTGCGCGCGGAAGATACCGCGGTGTATTATTGCGCGCGCTATTAT
     L  Q  M  N  S  L  R  A  E  D  T  A  V  Y  Y  C  A  R  Y  Y
                                                        ◄─────

301 TATTATTATGGCATGGATGTGTGGGGCCAGGGCACCACCGTGACCGTGAGCAGC
     Y  Y  Y  G  M  D  V  W  G  Q  G  T  T  V  T  V  S  S
     ═══════════ CDR3 ═══════►
```

Fig.4D

Humanized Anti-PD-1  Abs-h-924  V$_K$

```
1   GAGATTGTCCTGACTCAGTCTCCCGCTACCCTTTCCTTGTCTCCAGGCGAACGGGCCACC
     E  I  V  L  T  Q  S  P  A  T  L  S  L  S  P  G  E  R  A  T

61  ATTAGCTGCCGCGGAAGCCAGAGCCTGTCCTCATACCTCGCTTGGTATCAACAGCGGCCT
     I  S  C  R  G  S  Q  S  L  S  S  Y  L  A  W  Y  Q  Q  R  P
                     ◄═══════ CDR1 ═══════►

121 GGACAGGCACCCAGGCTGCTGATCTACGACGTGAGCAACCGGGCCACAGGGATCCCCGCC
     G  Q  A  P  R  L  L  I  Y  D  V  S  N  R  A  T  G  I  P  A
                              ◄═══════ CDR2 ═══════►

181 CGGTTTAGTGGGAGCGGTAGCGGCACAGATTTCACTCTGACCATCAGCGGCCTGGAACCC
     R  F  S  G  S  G  S  G  T  D  F  T  L  T  I  S  G  L  E  P

241 GAGGACTTCGCCGTGTACTATTGCCAGCAGCGGACCAACTGGCCCAGAGCCTTCGGCCAA
     E  D  F  A  V  Y  Y  C  Q  Q  R  T  N  W  P  R  A  F  G  Q
                              ◄═══════════ CDR3 ═══════════►

301 GGCACGAAGGTGGAGATCAAGCGGACCGTG
     G  T  K  V  E  I  K  R  T  V
```

Fig.5A

Rabbit Anti-PD-1 Abs-r-925 V$_H$

```
1   TGCCAGAGCCTGGAAGAAAGCGGCGGCGGCCTGGTGCAGCCGGGCACCACCCTGACCCTG
     C  Q  S  L  E  E  S  G  G  G  L  V  Q  P  G  T  T  L  T  L

61  AGCTGCACCGTGAGCGGCTTTACCCTGAGCAGCTATGCGATGATGTGGGTGCGCCAGGCG
     S  C  T  V  S  G  F  T  L  S  S  Y  A  M  M  W  V  R  Q  A
                     ←————— CDR1 —————→

121 CCGGGCAAAGGCCTGGAATGGATTGGCGTGATTAGCTATGATGGCAGCAACAAATATTAT
     P  G  K  G  L  E  W  I  G  V  I  S  Y  D  G  S  N  K  Y  Y
                                  ←————— CDR2 —————→

181 GCGCAGAGCGTGAAAGGCCGCTTTACCATTAGCCGCAACACCAGCCAGAACACCGTGACC
     A  Q  S  V  K  G  R  F  T  I  S  R  N  T  S  Q  N  T  V  T

241 CTGAAAATGACCAGCCTGACCGCGGAAGATACCGCGACCTATTTTTGCGCGCGCTATTAT
     L  K  M  T  S  L  T  A  E  D  T  A  T  Y  F  C  A  R  Y  Y
                                                           ←——

301 TATTATTATTATATGGATGTGTGGGGCCCGGTGACCGTGAGCAGC
     Y  Y  Y  Y  M  D  V  W  G  P  V  T  V  S  S
     ————— CDR3 —————→
```

Fig.5B

Rabbit Anti-PD-1 Abs-r-925 V$_K$

```
1   GAACTGGTGCTGACCCAGACCCCGAGCAGCGTGAGCGCGGCGGTGGGCGGCACCGTGACC
     E  L  V  L  T  Q  T  P  S  S  V  S  A  A  V  G  G  T  V  T

61  ACAATTACCTGCCGCGCGAGCCAGAGCGTGAGCAGCTATCTGGCGTGGTATCAGCAGAAA
     T  I  T  C  R  A  S  Q  S  V  S  S  Y  L  A  W  Y  Q  Q  K
                         ←————— CDR1 —————→

121 CCGGGCCAGGCGCCGAAACTGCTGATTTATGAAGCGAGCAACCGCGCGACCGGCGTGCCG
     P  G  Q  A  P  K  L  L  I  Y  E  A  S  N  R  A  T  G  V  P
                                  ←————— CDR2 —————→

181 AGCCGCTTTAGCGGCAGCGGCAGCGGCACCGAATTTACCCTGACCATTAGCGGCGTGCAG
     S  R  F  S  G  S  G  S  G  T  E  F  T  L  T  I  S  G  V  Q

241 TGCGATGATGCGACCTATTATTGCCAGCAGCGCACCAACTGGCCGCCGGCGTTTGGCGGC
     C  D  D  A  T  Y  Y  C  Q  Q  R  T  N  W  P  P  A  F  G  G
                              ←————— CDR3 —————→

301 GGCACCAAAGTGGTGGTGAAAGGCGATCCG
     G  T  K  V  V  V  K  G  D  P
```

Fig.5C

Humanized Anti-PD-1 Abs-h-925 V$_H$

```
1   CAGGTGCAGCTGGTGGATAGCGGCGGCGGCGTGGTGCAGCCGGGCCGCAGCCTGCGCCTG
      Q  V  Q  L  V  D  S  G  G  G  V  V  Q  P  G  R  S  L  R  L

61  AGCTGCGCGGCGAGCGCGTTTACCTTTAGCAGCTATGCGATGCATTGGGTGCGCCAGGCG
      S  C  A  A  S  A  F  T  F  S  S  Y  A  M  H  W  V  R  Q  A
                      <------- CDR1 ------->

121 CCGGGCAAAGGCCTGGAATGGGTGGCGGTGATTAGCTATGATGGCAGCAACAAATATTAT
      P  G  K  G  L  E  W  V  A  V  I  S  Y  D  G  S  N  K  Y  Y
                                  <----- CDR2 ----->

181 GCGGATAGCGTGAAAGGCCGCTTTACCATTAGCCGCGATAACAGCAAAAACACCCTGTAT
      A  D  S  V  K  G  R  F  T  I  S  R  D  N  S  K  N  T  L  Y

241 CTGCAGATGAACAGCCTGCGCGCGGAAGATACCGCGGTGTATTATTGCGCGCGCTATTAT
      L  Q  M  N  S  L  R  A  E  D  T  A  V  Y  Y  C  A  R  Y  Y

301 TATTATTATTATATGGATGTGTGGGGCAAAGGCACCACCGTGACCGTGAGCAGC
      Y  Y  Y  Y  M  D  V  W  G  K  G  T  T  V  T  V  S  S
      <------ CDR3 ------>
```

Fig.5D

Humanized Anti-PD-1 Abs-h-925 V$_K$

```
1   GAGATCGTGCTGACGCAATCACCCGCCACCCTGAGCCTGTCCCCTGGCGAGCGGGCTACA
      E  I  V  L  T  Q  S  P  A  T  L  S  L  S  P  G  E  R  A  T

61  CTGAGCTGCCGGGCCAGTCAGTCAGTGAGCAGTTACTTGGCTTGGTACCAGCAGAAACCC
      L  S  C  R  A  S  Q  S  V  S  S  Y  L  A  W  Y  Q  Q  K  P
                          <---- CDR1 ---->

121 GGCCAAGCCCCACGGCTGCTTATTTATGAGGCATCCAACAGAGCGACCGGCATCCCTGCC
      G  Q  A  P  R  L  L  I  Y  E  A  S  N  R  A  T  G  I  P  A
                                  <--- CDR2 --->

181 CGCTTCTCTGGCTCTGGATCCGGGACCGACTTCACTCTCACTATCAGCAGCCTGGAACCC
      R  F  S  G  S  G  S  G  T  D  F  T  L  T  I  S  S  L  E  P

241 GAGGACTTCGCAGTCTATTACTGCCAGCAGAGGACCAACTGGCCCCCAGCCTTTGGTCAG
      E  D  F  A  V  Y  Y  C  Q  Q  R  T  N  W  P  P  A  F  G  Q
                              <-------- CDR3 -------->

301 GGCACAAAGGTGGAAATCAAGCGGACCGTG
      G  T  K  V  E  I  K  R  T  V
```

Fig.6A

Rabbit Anti-PD-1   Abs-r-926 $V_H$

```
1   TGCCAGAGCGTGGAAGAAAGCGGCGGCGGCCTGGTGAAACCGACCGATACCCTGACCCTG
    C  Q  S  V  E  E  S  G  G  G  L  V  K  P  T  D  T  L  T  L

61  ACCTGCACCGTGAGCGGCATTAGCCTGAGCAGCTATTATTGGAGCTGGGTGCGCCAGGCG
    T  C  T  V  S  G  I  S  L  S  S  Y  Y  W  S  W  V  R  Q  A
                    ←――――― CDR1 ―――――→

121 CCGGGCAAAGGCCTGGAATGGATTGGCTATATTTATTATAGCGGCAGCGGCACCAACTAT
    P  G  K  G  L  E  W  I  G  Y  I  Y  Y  S  G  S  G  T  N  Y
                                ←――――― CDR2 ―――――→

181 AACCCGAGCCTGAAAAGCCGCAGCACCATTAGCCGCAACACCAACACCAACACCGTGACC
    N  P  S  L  K  S  R  S  T  I  S  R  N  T  N  T  N  T  V  T

241 CTGAAAATGACCAGCCTGACCGCGGCGGATACCGCGACCTATTATTGCGCGCGCTGGTAT
    L  K  M  T  S  L  T  A  A  D  T  A  T  Y  Y  C  A  R  W  Y
                                                        ←――――

301 TTTGATCTGTGGGGCCAGGGCACCCTGGTGACCGTGAGCAGC
    F  D  L  W  G  Q  G  T  L  V  T  V  S  S
        CDR3
```

Fig.6B

Rabbit Anti-PD-1   Abs-r-926  $V_K$

```
1   GAAATTGTGCTGACCCAGAGCCCGAGCAGCGTGAGCGTGAGCGTGGGCAGCACCGTGACC
    E  I  V  L  T  Q  S  P  S  S  V  S  V  S  V  G  S  T  V  T

61  ACAATTAACTGCCGCGCGAGCAACAGCGTGAGCAGCAGCCTGGCGTGGTATCAGCAGAAA
    T  I  N  C  R  A  S  N  S  V  S  S  S  L  A  W  Y  Q  Q  K
                          ←――――― CDR1 ―――――→

121 CCGGGCCAGGCGCCGCGCCTGCTGATTTATGATACCAGCAACCGCGAAACCGGCGTGCCG
    P  G  Q  A  P  R  L  L  I  Y  D  T  S  N  R  E  T  G  V  P
                                  ←――――― CDR2 ―――――→

181 AGCCGCTTTAGCGGCAGCCGCAGCGGCACCGAATTTACCCTGACCATTAGCGGCGTGCAG
    S  R  F  S  G  S  R  S  G  T  E  F  T  L  T  I  S  G  V  Q

241 TGCGCGGATGCGGCGACCTATTATTGCCAGCAGCGCGATAACTGGCCGCGCGCGTTTGGC
    C  A  D  A  A  T  Y  Y  C  Q  Q  R  D  N  W  P  R  A  F  G
                                  ←――――― CDR3 ―――――→

301 GGCGGCACCAAAGTGGTGGTGAAACGCGATGTG
    G  G  T  K  V  V  V  K  R  D  V
```

Fig.6C

Humanized Anti-PD-1 Abs-h-926 V$_H$

```
1   CAGGTGCAGCTGCAGGAAAGCGGCCCGGGCCTGGTGAAACCGAGCGAAACCCTGAGCCTG
    Q   V   Q   L   Q   E   S   G   P   G   L   V   K   P   S   E   T   L   S   L

61  ACCTGCACCGTGAGCGGCGGCAGCATTAGCAGCTATTATTGGAGCTGGATTCGCCAGCCG
    T   C   T   V   S   G   G   S   I   S   S   Y   Y   W   S   W   I   R   Q   P
                        ←─────── CDR1 ───────→

121 CCGGGCAAAGGCCTGGAATGGATTGGCTATATTTATTATAGCGGCAGCACCAACTATAAC
    P   G   K   G   L   E   W   I   G   Y   I   Y   Y   S   G   S   T   N   Y   N
                                        ←─────────── CDR2 ───────────→

181 CCGAGCCTGAAAAGCCGCGTGACCATTAGCGTGGATACCAGCAAAAACCAGTTTAGCCT
    P   S   L   K   S   R   V   T   I   S   V   D   T   S   K   N   Q   F   S   L

241 AAACTGAGCAGCGTGACCGCGGCGGATACCGCGGTGTATTATTGCGCGTATTGGTATTTT
    K   L   S   S   V   T   A   A   D   T   A   V   Y   Y   C   A   Y   W   Y   F
                                                                ←─────── CDR3

301 GATCTGTGGGGCCGCGGCACCCTGGTGACCGTGAGCAGC
    D   L   W   G   R   G   T   L   V   T   V   S   S
    ──────→
```

Fig.6D

Humanized Anti-PD-1 Abs-h-926 V$_K$

```
1   GAGATTGTGCTGACTCAGTCCCCATCCACCCTGAGTCTGTCACCCGGACAGAAAGCCACT
    E   I   V   L   T   Q   S   P   S   T   L   S   L   S   P   G   Q   K   A   T

61  CTGTCTTGCAGAGCCAGCAATAGCGTCAGCTCAAGCCTGGCCTGGTATCAGCAGAAGCCC
    L   S   C   R   A   S   N   S   V   S   S   S   L   A   W   Y   Q   Q   K   P
                            ←─────── CDR1 ───────→

121 GGGAAAGCTCCCCGGCTTATGATCTACGACACCAGTAACCGGGAAACCGGCATCCCTGAG
    G   K   A   P   R   L   M   I   Y   D   T   S   N   R   E   T   G   I   P   E
                                        ←─────── CDR2 ───────→

181 CGCTTCAGCGGCTCTAAGTCTGGCACAGATTTCAGCCTCACAATCAGCTCCCTGGAGCCC
    R   F   S   G   S   K   S   G   T   D   F   S   L   T   I   S   S   L   E   P

241 GGTGACTTTGCCGTGTACTACTGCCAGCAGCGGGACAACTGGCCCCGGGCATTCGGCCAA
    G   D   F   A   V   Y   Y   C   Q   Q   R   D   N   W   P   R   A   F   G   Q
                                    ←─────────── CDR3 ───────────→

301 GGCACGAAGGTGACCATCAAGAGGACCGTG
    G   T   K   V   T   I   K   R   T   V
```

RECOMBINANT ANTIBODIES TO PROGRAMMED DEATH 1 (PD-1) AND USES THEREOF

CROSS REFERENCE TO RELATED APPLICATION

This application claims the benefit of priority under 35 U.S.C. § 371 of International Application No. PCT/IB2017/051275, filed on Mar. 4, 2017. The content of this earlier filed application is hereby incorporated by reference herein in its entirety.

SEQUENCE LISTING

The sequence listing submitted Aug. 26, 2019 as a text file named "13318_0045U1_Sequence_Listing," created on Aug. 22, 2019, and having a size of 31,475 bytes, is hereby incorporated by reference pursuant to 37 C.F.R. § 1.52(e)(5).

TECHNICAL FIELD

The present invention relates to antibodies that bind to programmed cell death 1 (PD-1) and particularly therapeutic and diagnostic methods of using those antibodies. The present invention belongs to the field of biotechnology.

BACKGROUND ART

In general, a need exists to provide safe and effective therapeutic methods for immune disorders such as, for example, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

An adaptive immune response involves activation, selection, and clonal proliferation of two major classes of lymphocytes termed T cells and B cells. After encountering an antigen, T cells proliferate and differentiate into antigen-specific effector cells, while B cells proliferate and differentiate into antibody-secreting cells.

T cell activation is a multi-step process requiring several signaling events between the T cell and an antigen-presenting cell (APC). For T cell activation to occur, two types of signals must be delivered to a resting T cell. The first type is mediated by the antigen-specific T cell receptor (TcR), and confers specificity to the immune response. The second, costimulatory, type regulates the magnitude of the response and is delivered through accessory receptors on the T cell.

A primary costimulatory signal is delivered through the activating CD28 receptor upon engagement of its ligands B7-1 or B7-2. In contrast, engagement of the inhibitory CTLA-4 receptor by the same B7-1 or B7-2 ligands results in attenuation of T cell response. Thus, CTLA-4 signals antagonize costimulation mediated by CD28. At high antigen concentrations, CD28 costimulation overrides the CTLA-4 inhibitory effect. Temporal regulation of the CD28 and CTLA-4 expression maintains a balance between activating and inhibitory signals and ensures the development of an effective immune response, while safeguarding against the development of autoimmunity.

Molecular homologues of CD28 and CTLA-4 and their B-7 like ligands have been recently identified. ICOS is a CD28-like costimulatory receptor. PD-1 (Programmed Death 1 or CD279) is an inhibitory receptor and a counterpart of CTLA-4. This disclosure relates to modulation of immune responses mediated by the PD-1 receptor.

PD-1 is a 50-55 kDa type I transmembrane receptor that was originally identified in a T cell line undergoing activation-induced apoptosis. PD-1 is expressed on activated T cells, B cells, and macrophages. The ligands for PD-1 are the B7 family members PD-L1 (B7-H1) and PD-L2 (B7-DC).

PD-1 is a member of the immunoglobulin (Ig) superfamily that contains a single Ig V-like domain in its extracellular region. The PD-1 cytoplasmic domain contains two tyrosines, with the most membrane-proximal tyrosine located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain.

Experimental data implicates the interactions of PD-1 with its ligands in down regulation of central and peripheral immune responses. In particular, proliferation in wild-type T cells but not in PD-1-deficient T cells is inhibited in the presence of PD-L1. Additionally, PD-1-deficient mice exhibit an autoimmune phenotype. PD-1 deficiency in the C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies.

Since PD-1 plays an important role in autoimmunity, tumor immunity and infectious immunity, it is an ideal target for immunotherapy. Blocking PD-1 with antagonists, including monoclonal antibodies, has been studied in treatments of cancer and chronic viral infections (Sheridan 2012, Nature Biotechnology 30: 729-730).

Monoclonal antibodies to PD-1 are known in the art and have been described, for example, in US Patent/Publication Nos. U.S. Pat. Nos. 8,008,449, 8,779,105, 9,084,776, 9,358,289, 9,387,247, US20090217401, US20130133091, US20140212422, US20140294852, US20140328833, US20140348743, US20150165025, and WO Patent/Publication Nos. WO2006121168, WO20091154335, WO2012145493, WO2013014668, WO2009101611, EP2262837, and EP2504028.

SUMMARY OF INVENTION

The present invention relates to anti-PD-1 antibodies and methods of using the same.

The present disclosure provides antibodies that can act as agonists and/or antagonists of PD-1, thereby modulating immune responses regulated by PD-1. The disclosure further provides anti-PD-1 antibodies that comprise novel antigen-binding fragments. Anti-PD-1 antibodies of the invention are capable of:
(A) Specifically binding to PD-1, including human PD-1;
(B) Competeting PD-1 binding to Nivolumab;
(C) Blocking PD-1 interactions with its natural ligand(s); or
(D) Performing both functions.

In particular embodiments, the four antibodies derived and defined from rabbit and further be humanized comprise a heavy chain variable region (VH) and/or a light chain variable region (VL) and their Complementarity Determining Region (CDR) as summarized in Table below:

| Antibody | | Complementarity Determining Region | | | SEQ ID NO | Sequence Type |
|---|---|---|---|---|---|---|
| | | CDR1 | CDR2 | CDR3 | | |
| Part A. CDR domain sequence of PD-1 antibodies derived from rabbit | | | | | | |
| Abs-r-923 | $V_H$ | CDR-H1 | CDR-H2 | CDR-H3 | 1-3 | Protein |
| | $V_L$ | CDR-L1 | CDR-L2 | CDR-L3 | 13-15 | Protein |

-continued

| | | | | | |
|---|---|---|---|---|---|
| Abs-r-924 | V_H | CDR-H1 | CDR-H2 | CDR-H3 | 4-6 Protein |
| | V_L | CDR-L1 | CDR-L2 | CDR-L3 | 16-18 Protein |
| Abs-r-925 | V_H | CDR-H1 | CDR-H2 | CDR-H3 | 7-9 Protein |
| | V_L | CDR-L1 | CDR-L2 | CDR-L3 | 19-21 Protein |
| Abs-r-926 | V_H | CDR-H1 | CDR-H2 | CDR-H3 | 10-12 Protein |
| | V_L | CDR-L1 | CDR-L2 | CDR-L3 | 22-24 Protein |
| Part B. CDR domain sequence of Humanized PD-1 antibodies | | | | | |
| Abs-h-923 | V_H | CDR-H1 | CDR-H2 | CDR-H3 | 25-27 Protein |
| | V_L | CDR-L1 | CDR-L2 | CDR-L3 | 37-39 Protein |
| Abs-h-924 | V_H | CDR-H1 | CDR-H2 | CDR-H3 | 28-30 Protein |
| | V_L | CDR-L1 | CDR-L2 | CDR-L3 | 40-42 Protein |
| Abs-h-925 | V_H | CDR-H1 | CDR-H2 | CDR-H3 | 31-33 Protein |
| | V_L | CDR-L1 | CDR-L2 | CDR-L3 | 43-45 Protein |
| Abs-h-926 | V_H | CDR-H1 | CDR-H2 | CDR-H3 | 34-36 Protein |
| | V_L | CDR-L1 | CDR-L2 | CDR-L3 | 46-48 Protein |

| Antibody | Variable Region | SEQ ID NO | Sequence Type |
|---|---|---|---|
| Part C. A full variable sequence of PD-1 antibodies derived from rabbit | | | |
| Abs-r-923 | Heavy Chian (V_H) | 49 | DNA |
| | Heavy Chian (V_H) | 50 | Protein |
| | Light Chian (V_L) | 51 | DNA |
| | Light Chian (V_L) | 52 | Protein |
| Abs-r-924 | Heavy Chian (V_H) | 53 | DNA |
| | Heavy Chian (V_H) | 54 | Protein |
| | Light Chian (V_L) | 55 | DNA |
| | Light Chian (V_L) | 56 | Protein |
| Abs-r-925 | Heavy Chian (V_H) | 57 | DNA |
| | Heavy Chian (V_H) | 58 | Protein |
| | Light Chian (V_L) | 59 | DNA |
| | Light Chian (V_L) | 60 | Protein |
| Abs-r-926 | Heavy Chian (V_H) | 61 | DNA |
| | Heavy Chian (V_H) | 62 | Protein |
| | Light Chian (V_L) | 63 | DNA |
| | Light Chian (V_L) | 64 | Protein |
| Part D. A full variable sequence of humanized PD-1 antibodies | | | |
| Abs-h-923 | Heavy Chian (V_H) | 65 | DNA |
| | Heavy Chian (V_H) | 66 | Protein |
| | Light Chian (V_L) | 67 | DNA |
| | Light Chian (V_L) | 68 | Protein |
| Abs-h-924 | Heavy Chian (V_H) | 69 | DNA |
| | Heavy Chian (V_H) | 70 | Protein |
| | Light Chian (V_L) | 71 | DNA |
| | Light Chian (V_L) | 72 | Protein |
| Abs-h-925 | Heavy Chian (V_H) | 73 | DNA |
| | Heavy Chian (V_H) | 74 | Protein |
| | Light Chian (V_L) | 75 | DNA |
| | Light Chian (V_L) | 76 | Protein |
| Abs-h-926 | Heavy Chian (V_H) | 77 | DNA |
| | Heavy Chian (V_H) | 78 | Protein |
| | Light Chian (V_L) | 79 | DNA |
| | Light Chian (V_L) | 80 | Protein |

DESCRIPTION OF EMBODIMENTS

In general, the present invention provides rabbit antibodies and antigen-binding fragments thereof that bind to PD-1, specifically in which they are recombinant antibody and also humanized antibodies.

In one aspect, the invention provides an rabbit antibody and antigen-binding fragments which specifically binds to human PD-1, and comprising a heavy chain variable region (H-CVR) selected from the group consisting of SEQ ID NOs:1-3 (H-CDR1, H-CDR2 and H-CDR3) and/or a light chain variable region (L-CVR) selected from the group consisting of SEQ ID NOs:13-15 (L-CDR1, L-CDR2 and L-CDR3).

In other aspect, the invention provides an rabbit antibody and antigen-binding fragments which specifically binds human PD-1, and comprising a heavy chain variable region (H-CVR) selected from the group consisting of SEQ ID NOs:4-6 (H-CDR1, H-CDR2 and H-CDR3) and/or a light chain variable region (L-CVR) selected from the group consisting of SEQ ID NOs:16-18 (L-CDR1, L-CDR2 and L-CDR3).

In another aspect, the invention provides an rabbit antibody and antigen-binding fragments which specifically binds human PD-1, and comprising a heavy chain variable region (H-CVR) selected from the group consisting of SEQ ID NOs:7-9 (H-CDR1, H-CDR2 and H-CDR3) and/or a light chain variable region (L-CVR) selected from the group consisting of SEQ ID NOs:19-21 (L-CDR1, L-CDR2 and L-CDR3).

In other aspect, the invention provides an rabbit antibodies and antigen-binding fragments which specifically bind human PD-1, and comprising a heavy chain variable region (H-CUR) selected from the group consisting of SEQ ID NOs:11-12 (H-CDR1, H-CDR2 and H-CDR3) and/or a light chain variable region (L-CVR) selected from the group consisting of SEQ ID NOs:22-24 (L-CDR1, L-CDR2 and L-CDR3).

Preferably, the rabbit anti-PD-1 antibodies of the invention are selected from Abs-r-923, Abs-r-924, Abs-r-925 and Abs-r-926.

In a preferred embodiments, the present invention provides an anti-PD-1 antibodies or antigen-binding fragments which are claimed as rabbit antibodies or fragments.

In a further preferred embodiments, the present invention provides a rabbit antibodies or fragments which comprise a heavy chain variable region (H-CVR) further containing rabbit IgG or its variant with heavy chain FR region.

In a further preferred embodiments, the present invention provides an rabbit antibodies or fragments which further contain rabbit IgG or its variant with heavy chain constant region.

In a preferred embodiments, the present invention provides a rabbit antibodies or fragments which comprise a light chain variable region (L-CVR) further containing rabbit k chain or its variant with light chain FR region.

In a further preferred embodiments, the present invention provides an rabbit antibodies or fragments which further contain rabbit IgG or its variant with light chain constant region.

In a preferred embodiments, the present invention provides an anti-PD-1 antibodies or antigen-binding fragments which comprise chimeric antibody or fragments.

In a further preferred embodiments, the present invention provides an chimeric antibody or fragments, and comprising a heavy chain variable region (H-CVR) from SEQ ID NOs: 50, 54, 58 and 62.

In a further preferred embodiments, the present invention provides an chimeric antibody or fragments, and comprising a light chain variable region (L-CVR) from SEQ ID NOs: 52, 56, 60 and 64.

In one aspect, the invention provides an humanized antibody or antigen-binding fragments which specifically binds to human PD-1, and comprising a heavy chain variable region (H-CVR) selected from the group consisting of SEQ ID NOs:25, 26 and 27 (H-CDR1, H-CDR2 and H-CDR3) and/or their variants, and/or a light chain variable region (L-CVR) selected from the group consisting of SEQ ID NOs:37, 38 and 39(L-CDR1, L-CDR2 and L-CDR3) or their variants.

In other aspect, the invention provides an humanized antibody or antigen-binding fragments which specifically binds human PD-1, and comprising a heavy chain variable region (H-CVR) selected from the group consisting of SEQ ID NOs: 28, 29 and 30 (H-CDR1, H-CDR2 and H-CDR3) and/or their variants, and/or a light chain variable region (L-CVR) selected from the group consisting of SEQ ID NOs: 40, 41 and 42 (L-CDR1, L-CDR2 and L-CDR3).

In other aspect, the invention provides an humanized antibody or antigen-binding fragments which specifically binds human PD-1, and comprising a heavy chain variable region (H-CVR) selected from the group consisting of SEQ ID NOs: 31, 32 and 33 (H-CDR1, H-CDR2 and H-CDR3) and/or their variants, and/or a light chain variable region (L-CVR) selected from the group consisting of SEQ ID NOs: 43, 44 and 45 (L-CDR1, L-CDR2 and L-CDR3).

In other aspect, the invention provides an humanized antibody or antigen-binding fragments which specifically binds human PD-1, and comprising a heavy chain variable region (H-CVR) selected from the group consisting of SEQ ID NOs: 34, 35 and 36 (H-CDR1, H-CDR2 and H-CDR3) and/or their variants, and/or a light chain variable region (L-CVR) selected from the group consisting of SEQ ID NOs: 46, 47 and 48 (L-CDR1, L-CDR2 and L-CDR3).

Preferably, the humanized anti-PD-1 antibodies of the invention are selected from Abs-h-923, Abs-h-924, Abs-h-925 and Abs-h-926.

In a preferred embodiments, the present invention provides an anti-PD-1 antibodies or antigen-binding fragments which are claimed as humanized antibodies or fragments.

In a further preferred embodiments, the present invention provides an humanized antibodies or fragments which comprise a heavy chain variable region (H-CVR) further containing human IgG1, IgG2, IgG3, IgG4 and/or a heavy chain FR region variant.

In a further preferred embodiments, the present invention provides an antibodies or fragments which further contain humanized antibody and/or a heavy chain constant region.

In a preferred embodiments, the present invention provides an humanized antibodies or fragments which comprise a light chain variable region (L-CVR) further containing human k, λ chain or a light chain FR region variant.

In a further preferred embodiments, the present invention provides an humanized antibodies or fragments which further contain human IgG and/or a light chain constant region variant.

In a preferred embodiments, the present invention provides an anti-PD-1 antibodies or antigen-binding fragments which comprise chimeric antibody or fragments, further containing human IgG1, IgG2, IgG3, IgG4 and/or a heavy chain constant variant, preferred human IgG1 or IgG4.

In a further preferred embodiments, the present invention provides an chimeric antibody or fragments, and comprising a heavy chain variable region (H-CVR) from SEQ ID NOs: 66, 70, 74 and 78.

In a further preferred embodiments, the present invention provides an chimeric antibody or fragments, and comprising a light chain variable region (L-CVR) from SEQ ID NOs: 68, 72, 76 and 80.

In some embodiments, the present invention provides an anti-PD-1 antibody or fragments, consisting of Fab, Fv, single chain variable fragment (scFv), F(ab')$_2$ and diabody.

In another aspect, the present invention provides an isolated nucleic acids, DNA molecules that encode any of the antibodies described herein.

In a further aspect, the present invention provides an isolated polynucleotide composition, comprising: an encoder of the present invention, the anti-PD-1 polynucleotide of the light chain of antibody or a functional fragment and the anti-PD-1 polynucleotide of the heavy chain of antibody or functional fragment thereof.

In another aspect, antibody or antigen binding portion of the invention can be derivatized or linked to another functional molecule, e.g., another peptide or protein (e.g., another antibody or ligand receptor) to generate at least two different the bispecific binding sites or target molecules. Antibodies of the invention can in fact be derivatized or linked to more than one other functional molecule to generate more than two different binding sites and/or target molecule binding multispecific molecule; such multispecific molecules are also intended to be as used herein.

In another aspect, the present invention provides an expression vector of comprising the nucleic acids thereof encoding the present invention.

In a further aspect, the present invention provides an host cell of transfected expression vector.

In another embodiments of the present invention is provided comprising host cells. In certain the host cell is selected from mammalian cells, more specifically, the mammalian cell is selected from Chinese hamster ovary cells.

In some particular embodiments, according to the anti-PD-1 antibodies or functional fragments thereof of the present invention block the interaction and/or interact with PD-1 and PD-L2 and the PD-1 and PD-L1.

In a further aspect, the present invention provides the use according to the anti-PD-1 antibody or a functional fragment of the present invention in the manufacture of a medicament for enhancing the immune response of T cells. In some embodiments, the enhanced immune response includes enhancement of T cell cytokines, preferably the cytokine comprises IL-2.

In a further aspect, the present invention provides the use according to the anti-PD-1 antibody or a functional fragment of the present invention for competitively binding to human PD-1 with Nivolumab antibody. In particular embodiments, the competitive binding includes blocking binding of antibody to PD-1, preferably the antibody comprises Nivolumab.

In another aspect, the present invention provides the use according to the anti-PD-1 antibody or a functional fragment of the present invention for the treatment or prevention of cancer or infectious diseases of the medicament.

The present invention further provides a method of treating and preventing PD-1 mediated disease or disorder, or comprising pharmaceutical compositions thereof; preferably wherein said disease is cancer, most preferably the breast cancer, lung cancer, stomach cancer, colon cancer, kidney cancer and melanoma.

EXAMPLES

The following examples are provided to further explain and demonstrate some of the presently preferred embodiments and are not intended to limit the scope or content of the invention in any way.

Example-1: Generation of Rabbit Anti-PD-1 Antibodies

A. Immunization of Rabbit with PD-1

Four female rabbits aged 4 months were used for immunizations. The each rabbit was subcutaneously primed with 50 µg of own-made recombinant human PD-1 mixed well with complete Freund's adjuvant (Sigma-Aldrich, Cat #263810). Two to three weeks later, the rabbits were boosted with 25 µg of soluble PD-1 with incomplete Freund's adjuvant (Sigma-Aldrich, Cat #263910). The immune response was monitored by checked antiserum taken from rabbit's auricular vein blood. A serial dilutions of the antiserum from immunized animals were then screened for binding to the coated human PD-1 by ELISA. The same purified protein in PBS used for immunizations diluted to 1 µg/ml, was coated overnight microtiter plate (Nunc MAX-ISORP), 100 µl/well, incubated at 4° C. overnight, then blocked with 200 µl/well containing 5% fetal calf serum, PBS solution of 0.05% Tween 20. A serially diluted immunized sera were added to each well and incubated at room temperature for 1 hour. With PBS/Tween 20 solution washing the plate, horseradish peroxidase-conjugated goat anti-rabbit IgG antibody (Jackson Immunoresearch Labs, Cat #:111-035-046) was incubated for 1 hour at room temperature. After the plate was washed with washing buffer, 100 µl/well of TMB substrate was added, then (Pierce, Cat #34021) colored, stopped reaction and measured OD value at 450 nm.

B. Screening of Rabbit Anti-PD-1 Antibodies for Binding to Human PD-1

According to titer comparison, the rabbits with anti-PD-1 high titer immunoglobulin were chosen for isolation of rabbit PD-1-specific B cell. Cells were interrogated for antigen-specific B cells, unstimulated or stimulated, using LPS (Invivogen) at a concentration of 20 ng/mL. The cells, unstimulated or stimulated, were then loaded into pre-coated and blocked plate as described below. 384 well plate coated with anti-rabbit IgG antibody (Jackson Immunoresearch, Cat #111-005-008) was blocked with PBS solution containing 5% fetal calf serum and 0.05% Tween 20, then used to capture the antigen-specific B cells, contained the secreted output of the B cells. The antibodies secreted by the B cells in each well were then assayed for reactivity against human PD-1, or an unrelated antigen, and also assayed for IgG reactivity. Mainly, following three combined approaches were further applied for efficiently screened rabbit anti-PD-1 antibodies with blocking function and high binding affinity.

(i) Screening of Functional Anti-PD-1 Antibody by Fluorometric Microvolume Assay Technology, FMAT Recombinant antibodies from cultured supernatants were also used in cell-based binding studies. HEK293 cells were transfected with expression plasmids encoding the Ig heavy and light chains of rabbit anti-PD-1 antibodies. After 3-5 days, recombinant antibodies in the supernatants of transfected cells were harvested, Stable HEK293 cells expressing human PD-1 or primary cells were used for the cell-based binding confirmation studies. Antibodies from cultured supernatants were assessed for binding to cell surface PD-1 using fluorescently labeled anti-rabbit IgG antibody (Jackson Immunoresearch, Cat #111-095-046), Fluorescence microscopy studies revealed that a number of anti-PD-1 antibodies obtained from transfection supernatants bound to PD-1 expressed on the surface of HEK293 cells. In this screening assay, own-made anti-PD-1 antibody and isotype control rabbit IgG were used as controls. The FIG. 1A represents one of multiple 384-well plates detecting PD-1 antibodies from immunized rabbits that inhibit PD-1 function. Antibodies which show no inhibition are seen as signals above the plane of the graph. Antibodies that inhibit PD-1 function remain "flat" with the plane of the graph and represent the majority in FMAT screens. FIG. 1B further summarize results of tests of binding of various rabbit anti-PD-1 antibodies to PD-1 expressed on the surface of HEK293 cells. Four antibodies with desired inhibition function and biding affinity were selected and confirmed by other assays below.

(ii) Screening of Binding Anti-PD-1 Antibody by Enzyme-Linked Immunosorbent Assay, ELISA To begin the ELISA, 384-well plates were coated with human PD-1, blocked with assay diluent buffer, and washed, prior to incubation with serial dilutions of supernatants from the cultured PD-1-specific B-cells. The samples were incubated for one hour, and then the ELISA plates were washed. The detection goat anti-rabbit antibody-conjugated with HRP in the same assay diluent buffer, was then added, the assay plate was washed, and substrate solution was added to the wells in the assay plate. After the enzyme reaction was stopped, calorimetric density at 450 nm was measured in a conventional plate reader. Over hundred of PD-1-positive clones were screened by ELISA. Furthermore, the four of rabbit anti-PD-1 antibodies with specifically and strongly binding activity, named as Abs-r-923, Abs-r-924, Abs-r-925 and Abs-r-926 were defined and selected for characterizations (See in FIG. 1C). Binding data showed that they did not react with other unrelated proteins as coated, but also did not have cross-reactivity with mouse PD-1.

(iii) The Interaction of PD-1 with PD-L1 Blocked by Selected Anti-PD-1 Antibody (See Example 3 Below).

C. Isolation of PD-1 Antibodies that Bind to Human PD-1

Antibody-producing cells identified from screening above were used for isolated the genetic sequences encoding antibody heavy and light chains. The genes encoding the specific antibodies that recognize human PD-1 were retrieved using RT-PCR. Retrieved cells were placed into reverse transcription buffer, and the mRNA from each individual cell was reverse transcribed into cDNA. After generating these amplicons by standard nested polymerase chain reaction (PCR), these amplicons were subjected to direct sequencing. These DNA sequences were then bioinformatically filtered for sequence quality and organized into a sequence database for cladistics analysis, in order to identify how many unique antibody clades were isolated that recognize PD-1. According to the manufacturer's protocol, the amplified and selected sequences were cloned into HEK293 expression system for producing PD-1 antibody. Complete antibody variable regions comprising a pair of heavy ($V_H$) and light chain variable regions ($V_L$) were reformatted into plasmids with the proper elements for transient expression in mammalian cell lines, e.g., HEK293 using standard molecular biology techniques. For example, the variable heavy (SEQ ID NO:54) and variable light (SEQ ID NO:56) cDNA sequences were sub-cloned into the vector backbone. Supernatants from transiently transfected mammalian cell lines were used to test for antibody expression, specificity and affinity. Various $V_H$ and $V_L$ were paired to yield more than hundred of clones, in which 10 (a to j clones) of them were selected and expressed in HEK293 cells and assayed for PD-1 functional inhibition assay (See FIG. 1C). These analyses identified unique clades of sequences that recognize human PD-1. Selected sequences were sub-cloned into PCR 2.1 (LifeTech) for further propagation.

The sequences of the individual heavy chain and light chain variable regions are shown in FIGS. 3A, 4A, 5A and 6A (HCVR) and FIGS. 3B, 4B, 5B and 6B (LCVR). The complementarity determining regions (CDRs) and framework regions (FRs) are indicated as well. Tables 1, 2, 5, 6, 9, 10, 13 and 14 list each H-CDR or L-CDR by clone name and corresponding sequence identifier, Abs-r-923, Abs-r-924, Abs-r-925 and Abs-r-926. They are also described in PD-1 antibody sequence listing.

FIG. 1D also showed that an example of an ELISA-based binding assay. The results represent an average of two experiments. According to PD-1 antibody ability to block the binding of PD-L1, Abs-r-923, Abs-r-924, Abs-r-925 and Abs-r-926 clones are selected as a candidates for further development of a humanized antibody (See also in Example 2 below).

Example-2. Humanization of Rabbit Anti-PD-1 Antibodies

Humanization of selected rabbit anti-PD-1 antibodies was performed in order to reduce the apparent immunogenicity of the rabbit-based antibodies. Using antibody engineering information well-known in the art, and conventional bioinformatics tools, amino acid sequences of certain rabbit anti-PD-1 antibodies of the invention were analyzed and compared against known human antibody sequences. Based on these analyses and comparisons, certain human sequences were chosen for conventional rabbit CDR grafting, and inclusion of suitable back mutations. In tests for binding to human PD-1, these humanized antibodies were evaluated with respect to criteria such as function, affinity, avidity, binding kinetics, and biochemical behavior such as aggregation as well as expression levels.

A. Humanized Heavy Chain Variable Region Sequence

With the known human germline immunoglobulin heavy chain sequences are compared, selected low immunogenicity human germline framework sequence to finalize humanization of four rabbit PD-1 antibodies, Abs-r-923, Abs-r-924, Abs-r-925 and Abs-r-926. The DNA and amino add sequences of the four rabbit recombinant monoclonal antibodies are shown in FIGS. 3A, 4A, 5A and 6A, and also in SEQ ID NOs: 49, 50, 53, 54, 57, 58, 61 and 62, as well as further H-CDRs in Tables 1, 5, 9 and 13 below. See these sequences also in PD-1 antibody sequence listing.

The DNA and amino acid sequences of the heavy chain variable region of humanized Abs-h-923, Abs-h-924, Abs-h-925 and Abs-h-926 are shown in SEQ ID NOs: 65, 66, 69, 70, 73, 74, 77 and 78, and further H-CDR sequences in Tables 3, 7, 11 and 15. See these sequences also in PD-1 antibody sequence listing.

B. Humanized Light Chain Variable Region Sequence

With the known human germline immunoglobulin light chain sequences are compared, selected low immunogenicity human germline framework sequence to finalize humanization of four rabbit PD-1 antibodies, Abs-r-923, Abs-r-924, Abs-r-925 and Abs-r-926. The DNA and amino acid sequence of the light chain variable region of the four rabbit recombinant monoclonal antibodies are shown in FIGS. 3B, 4B, 5B and 6B, and also in SEQ ID NOs: 51, 52, 55, 56, 59, 60, 63 and 64, and further L-CDRs in Tables 2, 6, 10 and 14. See these sequences also in PD-1 antibody sequence listing.

The DNA and amino acid sequence of the light chain variable region of humanized Abs-h-923, Abs-h-924, Abs-h-925 and Abs-h-926 are shown in SEQ ID NOs: 67, 68, 71, 72, 75, 76, 79 and 80, and further L-CDRs in Tables 4, 8, 12 and 16. See these sequences also in PD-1 antibody sequence listing.

Example-3: Blocking of Humanized PD-1 Antibodies Binding to PD-L1

By blocking the PD-1 ligand binding manner of the present invention which is the humanized anti-PD-1 antibodies testing. Specifically, 100 µl of unlabeled human PD-L1 (R & D Systems, Cat #156-B7-100) was coated at a concentration of 1 µg/mL in PBS on a 96-well microtiter plates overnight at 4° C., Nonspecific binding sites were subsequently blocked using a 0.5% (w/v) solution of BSA and 0.05% (w/v) Tween 20 in PBS, In a blocking assay, a constant concentration of 1.5 nM (0.5 ug/ml) of human PD-1 protein was added to a serial dilutions of humanized anti-PD-1 antibodies or Nivolumab or isotype control antibody. The antibody-protein complexes with 1.5 nM constant human PD-1 were transferred to microtiter plates coated with human PD-L1. After incubating for 1 hour at RT, the wells were washed, and plate-bound human PD-1 was detected with an anti-human IgG Fc antibody conjugated with horseradish peroxidase (HRP) (Abcam, Cat #ab97225). After the plate was washed with washing buffer, 100 µl/well of TMB substrate was added, then colored, stopped reaction and measured OD value at 450 nm. As shown in FIG. 2, the humanized anti-PD-1 antibodies, Abs-h-923, Abs-h-924, Abs-h-925 and Abs-h-926 still maintained their functions and specifically blocked the binding of PD-1 to its ligand PD-L1, and significantly better than the blocking effect of Nivolumab. Thus, the antibody of the present invention achieves a surprisingly higher for PD-1 blocking the binding of PD-L1.

Example 4. Construction and Expression of a Fully Humanized PD-1 Antibody

Human IgG4 heavy chain constant region fragment IgG4 Fc sequence and κ light chain constant region fragment sequences were synthesized by the company IDT (Integrated DNA Technologies, Coralville, Iowa) respectively, then put to pcDNA3 vector backbone to pBA-H4 and pBA-Ck of the present invention, pBA-H4 (containing human IgG4 heavy chain constant region IgG4Fc) and pBA-Ck (containing the human K light chain constant region fragment) vector built by Bioabs company, using the CMV promoter pBA-H4 in VH and CH, puromycin resistance gene use PGK promoter, in pBA-Ck in VL use CMV promoter, neomycin resistance gene SV40 promoter. According to the protein sequence of the antibody heavy chain variable region sequence and light chain variable region encoding the heavy chain and light design chain variable region DNA sequences, and in accordance with optimizing expression in CHO cells, and further optimize the DNA sequences encoding the heavy and light chain variable region, wherein the encoding of the present invention is the humanized anti-PD-1 antibody heavy chain variable region DNA sequences are shown in SEQ ID NOs: 65 (Abs-h-923), 69 (Abs-h-924), 73 (Abs-h-925) and 77 (Abs-h-926), the present invention encoding the humanized anti-PD-1 antibody light chain variable region DNA sequence as SEQ ID NOs: 67 (Abs-h-923), 71 (Abs-h-924), 75 (Abs-h-925) and 79 (Abs-h-926). All tested PD-1 antibodies were purified by protein A column containing suitable resin, MabSelect™ from GE Healthcare.

Example 5. Specificity and Affinity of Humanized PD-1 Antibodies

The binding affinity of the anti-PD-1 antibodies Abs-h-923, Abs-h-924, Abs-h-925 and Abs-h-926 were determined by surface plasmon resonance (SPR) using the Biacore™ technology. This technology allows the label-free determination of the microscopic rate constants for binding ($k_a$) and dissociation ($k_d$) of a ligand to a receptor. It is therefore especially suited for characterizing the antibody-antigen interactions. Indirect binding of antibodies to the Biacore™ chip surface was done via an anti-human IgG antibody (GE Healthcare Bio-Sciences AB; Cat #BR-1008-39) 25 pg/ml in immobilization buffer (10 mM Sodium acetate pH 5.0). Anti-PD-1 antibody in 2-fold increasing concentrations from 0.14 to 7.68 nM was diluted into assay buffer to measure affinity of Abs-h-923, Abs-h-924, Abs-h-925 and Abs-h-926. The kinetic traces were evaluated with the Biacore™ T2000. The full set of these traces with increasing concentrations is taken together and is called a run. Two zero concentration samples (blank runs) were included in each analyte concentration series to allow double-referencing during data evaluation. The kinetic rate constants for association ($k_a$) and dissociation ($k_d$) as well as the dissociation equilibrium constant ($K_D$) were calculated. The affinity data of Abs-h-923, Abs-h-924, Abs-h-925 and Abs-h-926 are shown in Table 17.

Example 6. Competitive Binding of Humanized PD-1 Antibodies with Nivolumab

Competitive binding analysis was performed on humanized antibodies, Abs-h-923, Abs-h-924, Abs-h-925 and Abs-h-926 with Nivolumab, using ELISA-based assay. The assay was conducted essentially as follows. A different of concentration of PD-1 antibodies, Abs-h-923, Abs-h-924, Abs-h-925 and Abs-h-926 were pre-incubated with constant concentration, 50 ng/ml of Nivolumab or an isotype antibody (negative control) for 1 hour at 37° C. The mixtures were added into 96-well plate coated human PD-1 at concentration of 100 ng/well and further incubated for other hour, then washed. HRP-conjugated anti-human antibody was added and incubated. After the plate was washed with washing buffer, 100 μl/well of TMB substrate was added, then (Pierce, Cat #34021) colored, stopped reaction and measured OD value at 450 nm.

All humanized antibodies competitively inhibited the binding of Nivolumab to PD-1. However, antibody Abs-h-923 performed weak competition binding to PD-1. Antibody Abs-h-926 had the highest competition activity compared to the other three. In contrast, isotype antibody did not competitively inhibit binding of Nivolumab to PD-1 at all. Representative results are shown in FIG. 7.

The $EC_{50}$ of Abs-h-923, Abs-h-924, Abs-h-925 and Abs-h-926 is estimated by determining concentration of Abs-h-923, Abs-h-924, Abs-h-925 and Abs-h-926 that exhibit roughly one-half maximal absorbance from the point at which the Abs-h-923, Abs-h-924, Abs-h-925 and Abs-h-926 display saturation behavior (See Table 18).

Example 7. Humanized PD-1 Antibodies Induced IL-2 Cytokine Secretion in MLR Assays Increased secretion of IL-2 cytokine was observed in response to four antibodies Abs-h-923, Abs-h-924, Abs-h-925 and Abs-h-926 in mixed lymphocyte reaction (MLR) assays. One commercial stage anti-PD-1 antibody, Nivolumab was used as benchmarks for this experiment. The MLR assay was performed using commercially available monocyte-derived dendritic cells as stimulator cells and purified $CD4^+$ T lymphocytes as responder cells from a different healthy blood donor. Supernatants were collected at 2.5 days after beginning the assay. Cytokine secretion was measured in a capture sandwich immunoassay using MagPlex® microspheres (Luminex), according to the vendor's instructions.

FIG. 8 summarized the results of an MLR assay performed on human PBMCs treated with the anti-PD-1 antibodies. The data indicated that treatment with humanized PD-1 antibodies, Abs-h-924, Abs-h-925 and Abs-h-926 resulted in significantly increased secretion of cytokine IL-2, in comparison with antibody Nivolumab or the IgG4 isotype control (Biolegend). Interestingly, antibody Abs-h-923 showed weaker induced IL-2 response than other three antibodies Abs-h-924, Abs-h-925 and Abs-h-926. These data indicate that some of the anti-PD-1 antibodies of the present invention, e.g., Abs-h-926, induce increased IL-2 cytokine release in a manner similar to Nivolumab, while one antibody, Abs-h-923, elicits physiological responses that are measurably different from the responses elicited by Nivolumab.

TABLE 1

A H-CDR and full heavy chain variable sequences of rabbit anti-PD-1 antibody Abs-r-923

| No | Heavy Chain domain & Full Heavy Chain | Sequence & Note | Sequence Code |
|---|---|---|---|
| I | H-CDR1 | GFTLSSYA | SEQ ID NO: 1 |
| II | H-CDR2 | SNAGNGNT | SEQ ID NO: 2 |
| III | H-CDR3 | YWYFDL | SEQ ID NO: 3 |
| VI | DNA | See sequence listing and FIG. 3A | SEQ ID NO: 49 |
| V | Protein | The same above | SEQ ID NO: 50 |

TABLE 2

A L-CDR and full light chain variable sequences of rabbit anti-RD-1 antibody Abs-r-923

| No | Light Chain Domain & Full Light Chain | Sequence & Note | Sequence Code |
|---|---|---|---|
| I | L-CDR1 | QSGSSF | SEQ ID NO: 13 |
| II | L-CDR2 | ANNKRE | SEQ ID NO: 14 |

TABLE 2-continued

A L-CDR and full light chain variable sequences of rabbit anti-RD-1 antibody Abs-r-923

| No | Light Chain Domain & Full Light Chain | Sequence & Note | Sequence Code |
|---|---|---|---|
| III | L-CDR3 | GTYTDSPPT | SEQ ID NO: 15 |
| VI | DNA | See sequence listing and FIG. 3B | SEQ ID NO: 51 |
| V | Protein | The same above | SEQ ID NO: 52 |

TABLE-3

A H-CDR and full heavy chain variable sequence of humanized anti-PDA antibody Abs-h-923

| No | Heavy Chain domain & Full Heavy Chain | Sequence & Note | Sequence Code |
|---|---|---|---|
| I | H-CDR1 | GYTFTSYA | SEQ ID NO: 25 |
| II | H-CDR2 | SNAGNGNT | SEQ ID NO: 26 |
| III | H-CDR3 | YWYFDL | SEQ ID NO: 27 |
| VI | DNA | See sequence listing and FIG. 3C | SEQ ID NO: 65 |
| V | Protein | The same above | SEQ ID NO: 66 |

TABLE 4

A L-CDR and full light chain variable sequence of humanized anti-PD-1 antibody Abs-h-923

| No | Light Chain Domain & Full Light Chain | Sequence & Note | Sequence Code |
|---|---|---|---|
| I | L-CDR1 | QSGSSF | SEQ ID NO: 37 |
| II | L-CDR2 | ANNKRE | SEQ ID NO: 38 |
| III | L-CDR3 | GTYTDSPPT | SEQ ID NO: 39 |
| VI | DNA | See sequence listing and FIG. 3D | SEQ ID NO: 67 |
| V | Protein | The same above | SEQ ID NO: 68 |

TABLE 5

A H-CDR and full heavy chain variable sequences of rabbit anti-PD-1 antibody Abs-r-924

| No | Heavy Chain domain & Full Heavy Chain | Sequence & Note | Sequence Code |
|---|---|---|---|
| I | H-CDR1 | GFSISSYG | SEQ ID NO: 4 |
| II | H-CDR2 | ISYDGSNK | SEQ ID NO: 5 |
| III | H-CDR3 | YYYYYGMDV | SEQ ID NO: 6 |
| VI | DNA | See sequence listing and FIG. 4A | SEQ ID NO: 53 |
| V | Protein | The same above | SEQ ID NO: 54 |

TABLE 6

A L-CDR and full light chain variable sequences of rabbit anti-PD-1 antibody Abs-r-924

| No | Light Chain Domain & Full Light Chain | Sequence & Note | Sequence Code |
|---|---|---|---|
| I | L-CDR1 | QSLSSY | SEQ ID NO: 16 |
| II | L-CDR2 | DVSNRA | SEQ ID NO: 17 |
| III | L-CDR3 | QQRTNWPRA | SEQ ID NO: 18 |
| VI | DNA | See sequence listing and FIG. 4B | SEQ ID NO: 55 |
| V | Protein | The same above | SEQ ID NO: 56 |

TABLE-7

A H-CDR and full heavy chain variable sequence of humanized anti-PD-1 antibody Abs-h-924

| No | Heavy Chain domain & Full Heavy Chain | Sequence & Note | Sequence Code |
|---|---|---|---|
| I | H-CDR1 | GFTFSSYG | SEQ ID NO: 28 |
| II | H-CDR2 | ISYDGSNK | SEQ ID NO: 29 |
| III | H-CDR3 | YYYYYGMDV | SEQ ID NO: 30 |
| VI | DNA | See sequence listing and FIG. 4C | SEQ ID NO: 69 |
| V | Protein | The same above | SEQ ID NO: 70 |

TABLE 8

A L-CDR and full light chain variable sequence of humanized anti-PD-1 antibody Abs-h-924

| No | Light Chain Domain & Full Light Chain | Sequence & Note | Sequence Code |
|---|---|---|---|
| I | L-CDR1 | QSLSSY | SEQ ID NO: 40 |
| II | L-CDR2 | DVSNRA | SEQ ID NO: 41 |
| III | L-CDR3 | QQRTNWPRA | SEQ ID NO: 42 |
| VI | DNA | See sequence listing and FIG. 4D | SEQ ID NO: 71 |
| V | Protein | The same above | SEQ ID NO: 72 |

TABLE 9

A H-CDR and full heavy chain variable sequences of rabbit anti-PD-1 antibody Abs-r-925

| No | Heavy Chain domain & Full Heavy Chain | Sequence & Note | Sequence Code |
|---|---|---|---|
| I | H-CDR1 | GFTLSSYA | SEQ ID NO: 7 |
| II | H-CDR2 | ISYDGSNK | SEQ ID NO: 8 |
| III | H-CDR3 | YYYYYYMDV | SEQ ID NO: 9 |

TABLE 9-continued

A H-CDR and full heavy chain variable sequences of rabbit anti-PD-1 antibody Abs-r-925

| No | Heavy Chain domain & Full Heavy Chain | Sequence & Note | Sequence Code |
|---|---|---|---|
| VI | DNA | See sequence listing and FIG. 5A | SEQ ID NO: 57 |
| V | Protein | The same above | SEQ ID NO: 58 |

TABLE 10

A L-CDR and full light chain variable sequences of rabbit anti-PD-1 antibody Abs-r-925

| No | Light Chain Domain & Full Light Chain | Sequence & Note | Sequence Code |
|---|---|---|---|
| I | L-CDR1 | QSVSSY | SEQ ID NO: 19 |
| II | L-CDR2 | EASNRA | SEQ ID NO: 20 |
| III | L-CDR3 | QQRTNWPPA | SEQ ID NO: 21 |
| VI | DNA | See sequence listing and FIG. 5B | SEQ ID NO: 59 |
| V | Protein | The same above | SEQ ID NO: 60 |

TABLE 11

A H-CDR and full heavy chain variable sequence of humanized anti-PD-1 antibody Abs-h-925

| No | Heavy Chain domain & Full Heavy Chain | Sequence & Note | Sequence Code |
|---|---|---|---|
| I | H-CDR1 | AFTFSSYA | SEQ ID NO: 31 |
| II | H-CDR2 | ISYDGSNK | SEQ ID NO: 32 |
| III | H-CDR3 | YYYYYYMDV | SEQ ID NO: 33 |
| VI | DNA | See sequence listing and FIG. 5C | SEQ ID NO: 73 |
| V | Protein | The same above | SEQ ID NO: 74 |

TABLE 12

A L-CDR and full light chain variable sequence of humanized anti-PD-1 antibody Abs-h-925

| No | Light Chain Domain & Full Light Chain | Sequence & Note | Sequence Code |
|---|---|---|---|
| I | L-CDR1 | QSVSSY | SEQ ID NO: 43 |
| II | L-CDR2 | EASNRA | SEQ ID NO: 44 |
| III | L-CDR3 | QQRTNWPPA | SEQ ID NO: 45 |
| VI | DNA | See sequence listing and FIG. 5D | SEQ ID NO: 75 |
| V | Protein | The same above | SEQ ID NO: 76 |

TABLE 13

A H-CDR and full heavy chain variable sequences of rabbit anti-PD-1 antibody Abs-r-926

| No | Heavy Chain domain & Full Heavy Chain | Sequence & Note | Sequence Code |
|---|---|---|---|
| I | H-CDR1 | GISLSSYY | SEQ ID NO: 10 |
| II | H-CDR2 | IYYSGSTN | SEQ ID NO: 11 |
| III | H-CDR3 | WYFDL | SEQ ID NO: 12 |
| VI | DNA | See sequence listing and FIG. 6A | SEQ ID NO: 61 |
| V | Protein | The same above | SEQ ID NO: 62 |

TABLE 14

A L-CDR and full light chain variable sequences of rabbit anti-PD-1 antibody Abs-r-926

| No | Light Chain Domain & Full Light Chain | Sequence & Note | Sequence Code |
|---|---|---|---|
| I | L-CDR1 | NSVSSS | SEQ ID NO: 22 |
| II | L-CDR2 | DTSNRE | SEQ ID NO: 23 |
| III | L-CDR3 | QQRDNWPRA | SEQ ID NO: 24 |
| VI | DNA | See sequence listing and FIG. 6B | SEQ ID NO: 63 |
| V | Protein | The same above | SEQ ID NO: 64 |

TABLE 15

A H-CDR and full heavy chain variable sequence of humanized anti-PD-1 antibody Abs-h-926

| No | Heavy Chain domain & Full Heavy Chain | Sequence & Note | Sequence Code |
|---|---|---|---|
| I | H-CDR1 | GGSISSYY | SEQ ID NO: 34 |
| II | H-CDR2 | IYYSGSTN | SEQ ID NO: 35 |
| III | H-CDR3 | WYFDL | SEQ ID NO: 36 |
| VI | DNA | See sequence listing and FIG. 6C | SEQ ID NO: 77 |
| V | Protein | The same above | SEQ ID NO: 78 |

TABLE 16

A L-CDR and full light chain variable sequence of humanized anti-PD-1 antibody Abs-h-926

| No | Light Chain Domain & Full Light Chain | Sequence & Note | Sequence Code |
|---|---|---|---|
| I | L-CDR1 | NSVSSS | SEQ ID NO: 46 |
| II | L-CDR2 | DTSNRE | SEQ ID NO: 47 |
| III | L-CDR3 | QQRDNWPRA | SEQ ID NO: 48 |
| VI | DNA | See sequence listing and FIG. 6D | SEQ ID NO: 79 |
| V | Protein | The same above | SEQ ID NO: 80 |

TABLE 17

Binding affinity and kinetic rate constants of humanized PD-1 antibodies

| Antibody | Affinity | | |
|---|---|---|---|
| | $K_a$ (1/Ms) | $K_d$ (1/s) | $K_D$ (nM) |
| Abs-h-923 | 1.15E+6 | 7.9E−6 | 9.1E−12 |
| Abs-h-924 | 1.22E+6 | 3.9E−6 | 4.8E−12 |
| Abs-h-925 | 1.19E+6 | 3.2E−6 | 3.8E−12 |
| Abs-h-926 | 1.16E+6 | 2.1E−6 | 2.4E−12 |

TABLE 18

EC50 of humanized antibodies binding

| Antibody | EC50 (nM) |
|---|---|
| Abs-h-923 | 0.41 |
| Abs-h-924 | 0.14 |
| Abs-h-925 | 0.15 |
| Abs-h-926 | 0.18 |

REFERENCE TO DEPOSITED BIOLOGICAL MATERIAL

Not apply in this application.

SEQUENCE LISTING FREE TEXT

SEE PD-1 ANTIBODY SEQUENCE LISTING FILE

PATENT LITERATURE

PTL1: WO2013173223A1
PTL2: WO2015036394A1,
PTL3: WO2015112800A1,
PTL4: WO2015112900A1,
PTL5: WO2016020856A3₁
PTL6: WO2016068801A1
PTL7: WO2016077397A3
PTL8: WO2016106159A1
PTL9: U.S. Pat. No. 8,735,553 B1

NON PATENT LITERATURE

NPL1: Sharma P, Allison J P. Immune checkpoint targeting in cancer therapy: toward combination strategies with curative potential. Cell. 2015; 161(2):205-14.
NPL2: Webster R M. The immune checkpoint inhibitors: where are we now? Nat Rev Drug Discov. 2014; 13(12): 883-4.
NPL3: Garon E B, Rizvi N A, Hui R, Leighl N, Balmanoukian A S, Eder J P, et al. Pembrolizumab for the treatment of non-small-cell lung cancer. N Engl J Med. 2015; 372(21):2018-28
NPL4: Benson Jr D M, Bakan C E, Mishra A, Hofmeister C C, Efebera Y, Becknell B, et al. The PD-1/PD-L1 axis modulates the natural killer cell versus multiple myeloma effect: a therapeutic target for CT-011, a novel monoclonal anti-PD-1 antibody. Blood. 2010; 116(13):2286-94.
NPL5: Brahmer J, Reckamp K L, Baas P, Crino L, Eberhardt W E, Poddubskaya E, et al. Nivolumab versus docetaxel in advanced squamous-cell non-small-cell lung cancer. N Engl J Med. 2015; 373(2):123-35.

BRIEF DESCRIPTION OF DRAWINGS

The invention can be more completely understood with reference to the following drawings.

FIG. 3A shows DNA sequence (SEQ ID NO:49) and amino add sequence (SEQ ID NO:50) of Heavy Chain Variable Regions (H-CVR) from rabbit anti-human-PD-1 recombinant antibody, Abs-r-923. Complementarity determining regions of H-CDR1 through H-CDR3 are also shown in Table 1. It is further demonstrated in Example 3A of present invention.

FIG. 3B shows DNA sequence (SEQ ID NO:51) and amino acid sequence (SEQ ID NO:52) of Light Chain Variable Regions (L-CVR) from rabbit anti-human-PD-1 recombinant antibody, Abs-r-923. Complementarity determining regions of L-CDR1 through L-CDR3 are also shown in Table 2. It is further demonstrated in Example 3B of present invention.

FIG. 3C shows DNA sequence (SEQ ID NO:65) and amino acid sequence (SEQ ID NO:66) of Heavy Chain Variable Regions (H-CVR) from humanized anti-human-PD-1 recombinant antibody, Abs-h-923. Complementarity determining regions of H-CDR1 through H-CDR3 are also shown in Table 3. It is further demonstrated in Example 3A of present invention.

FIG. 3D shows DNA sequence (SEQ ID NO:67) and amino acid sequence (SEQ ID NO:68) of Light Chain Variable Regions (L-CVR) from humanized anti-human-PD-1 recombinant antibody, Abs-h-923. Complementarity determining regions of L-CDR1 through L-CDR3 are also shown in Table 4. It is further demonstrated in Example 3B of present invention.

FIG. 4A shows DNA sequence (SEQ ID NO:53) and amino acid sequence (SEQ ID NO:54) of Heavy Chain Variable Regions (H-CVR) from rabbit anti-human-PD-1 recombinant antibody, Abs-r-924. Complementarity determining regions of H-CDR1 through H-CDR3 are also shown in Table 5. It is further demonstrated in Example 3A of present invention.

FIG. 4B shows DNA sequence (SEQ ID NO:55) and amino acid sequence (SEQ ID NO:56) of Light Chain Variable Regions (L-CVR) from rabbit anti-human-PD-1 recombinant antibody, Abs-r-924. Complementarity determining regions of L-CDR1 through L-CDR3 are also shown in Table 6. It is further demonstrated in Example 3B of present invention.

FIG. 4C shows DNA sequence (SEQ ID NO:69) and amino acid sequence (SEQ ID NO:70) of Heavy Chain Variable Regions (H-CVR) from humanized anti-human-PD-1 recombinant antibody, Abs-h-924. Complementarity determining regions of H-CDR1 through H-CDR3 are also shown in Table 7. It is further demonstrated in Example 3A of present invention.

FIG. 4D shows DNA sequence (SEQ ID NO:71) and amino acid sequence (SEQ ID NO:72) of Light Chain Variable Regions (L-CVR) from humanized anti-human-PD-1 recombinant antibody, Abs-h-924. Complementarity determining regions of L-CDR1 through L-CDR3 are also shown in Table 8. It is further demonstrated in Example 3B of present invention.

FIG. 5A shows DNA sequence (SEQ ID NO:57) and amino acid sequence (SEQ ID NO:58) of Heavy Chain Variable Regions (H-CVR) from rabbit anti-human-PD-1 recombinant antibody, Abs-r-925. Complementarity determining regions of H-CDR1 through H-CDR3 are also shown in Table 9. It is further demonstrated in Example 3A of present invention.

FIG. 5B shows DNA sequence (SEQ ID NO:59) and amino acid sequence (SEQ ID NO:60) of Light Chain Variable Regions (L-CVR) from rabbit anti-human-PD-1 recombinant antibody, Abs-r-925. Complementarity determining regions of L-CDR1 through L-CDR3 are also shown in Table 10. It is further demonstrated in Example 3B of present invention.

FIG. 5C shows DNA sequence (SEQ ID NO:73) and amino acid sequence (SEQ ID NO:74) of Heavy Chain Variable Regions (H-CVR) from humanized anti-human-PD-1 recombinant antibody, Abs-h-925. Complementarity determining regions of H-CDR1 through H-CDR3 are also shown in Table 11. It is further demonstrated in Example 3A of present invention.

FIG. 5D shows DNA sequence (SEQ ID NO:75) and amino acid sequence (SEQ ID NO:76) of Light Chain Variable Regions (L-CVR) from humanized anti-human-PD-1 recombinant antibody, Abs-h-925. Complementarity determining regions of L-CDR1 through L-CDR3 are also shown in Table 12. It is further demonstrated in Example 3B of present invention.

FIG. 6A shows DNA sequence (SEQ ID NO:61) and amino acid sequence (SEQ ID NO:62) of heavy chain variable regions (H-CVR) from rabbit anti-human-PD-1 recombinant antibody, Abs-r-926. Complementarity determining regions of H-CDR1 through H-CDR3 are also shown in Table 13. It is further demonstrated in Example 3A of present invention.

FIG. 6B shows DNA sequence (SEQ ID NO:63) and amino acid sequence (SEQ ID NO:64) of Light Chain Variable Regions (L-CVR) from rabbit anti-human-PD-1 recombinant antibody, Abs-r-926. Complementarity determining regions of L-CDR1 through L-CDR3 are also shown in Table 14. It is further demonstrated in Example 3B of present invention.

FIG. 6C shows DNA sequence (SEQ ID NO:77) and amino acid sequence (SEQ ID NO:78) of Heavy Chain Variable Regions (H-CVR) from humanized anti-human-PD-1 recombinant antibody, Abs-h-926. Complementarity determining regions of H-CDR1 through H-CDR3 are also shown in Table 15. It is further demonstrated in Example 3A of present invention.

FIG. 6D shows DNA sequence (SEQ ID NO:79) and amino acid sequence (SEQ ID NO:80) of Light Chain Variable Regions (L-CVR) from humanized anti-human-PD-1 recombinant antibody, Abs-h-926. Complementarity determining regions of L-CDR1 through L-CDR3 are also shown in Table 16. It is further demonstrated in Example 3B of present invention.

SEQUENCE LISTING

<160> NUMBER OF SEQ ID NOS: 80

Figure 1A:
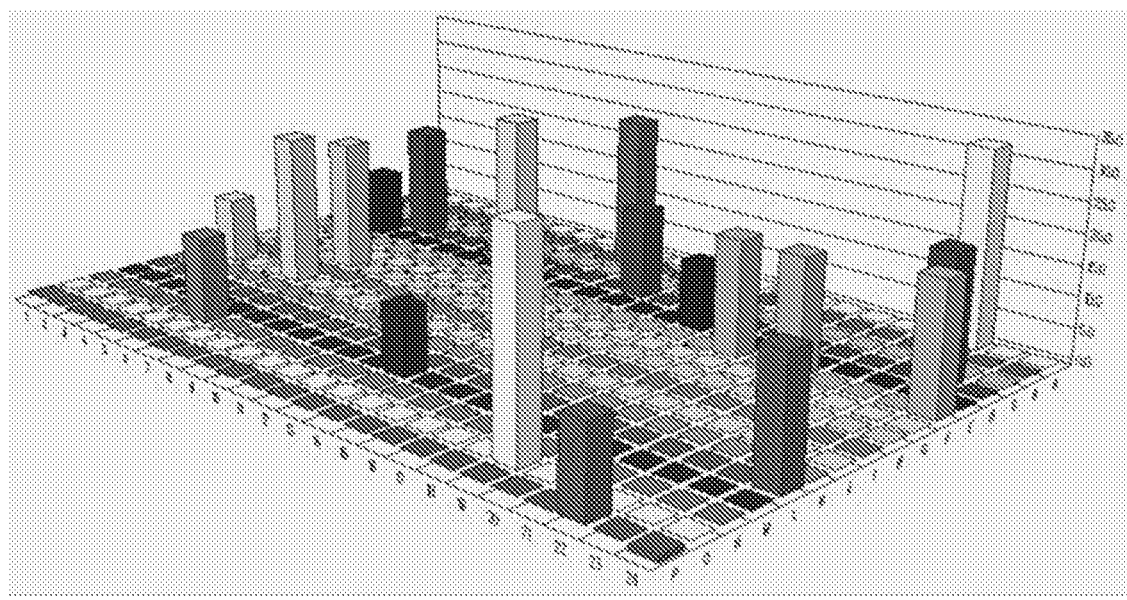
FIG. 1A shows summarizing data on specific and high-affinity binding of selected rabbit anti-human-PD-1 recombinant antibodies by FMAT assay. It is further demonstrated in Examples 1 and 3 of present invention.
Figure 1B:
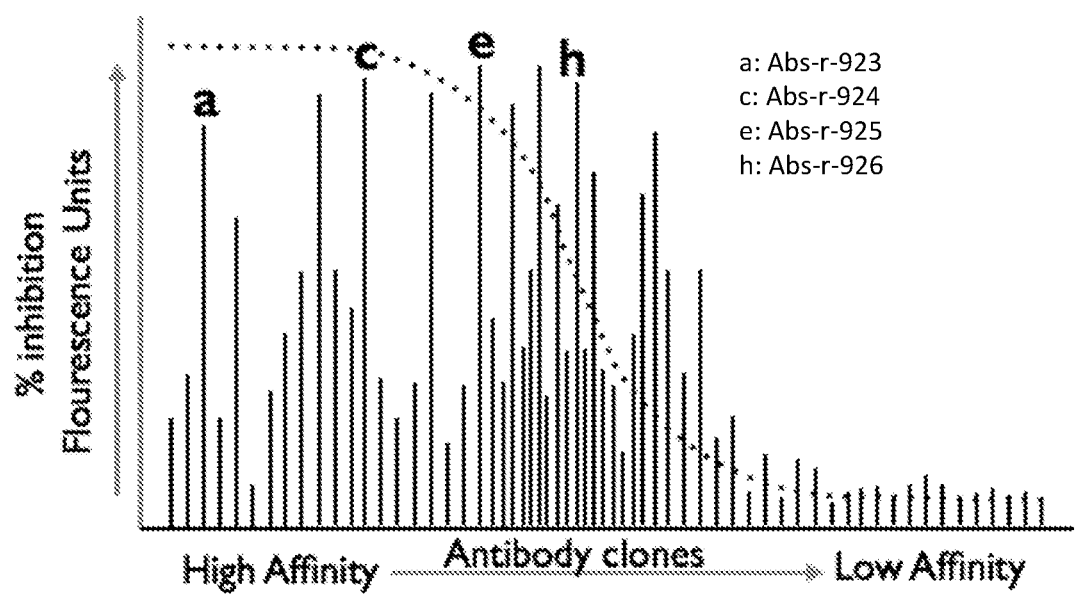
FIG. 1B shows summarizing data on both PD-1 inhibition function and binding affinity of selected rabbit anti-human-PD-1 recombinant antibodies, Abs-r-923, Abs-r-924, Abs-r-925 and Abs-r-926. It is further demonstrated in Examples 1 and 3 of present invention.
Figure 1C:
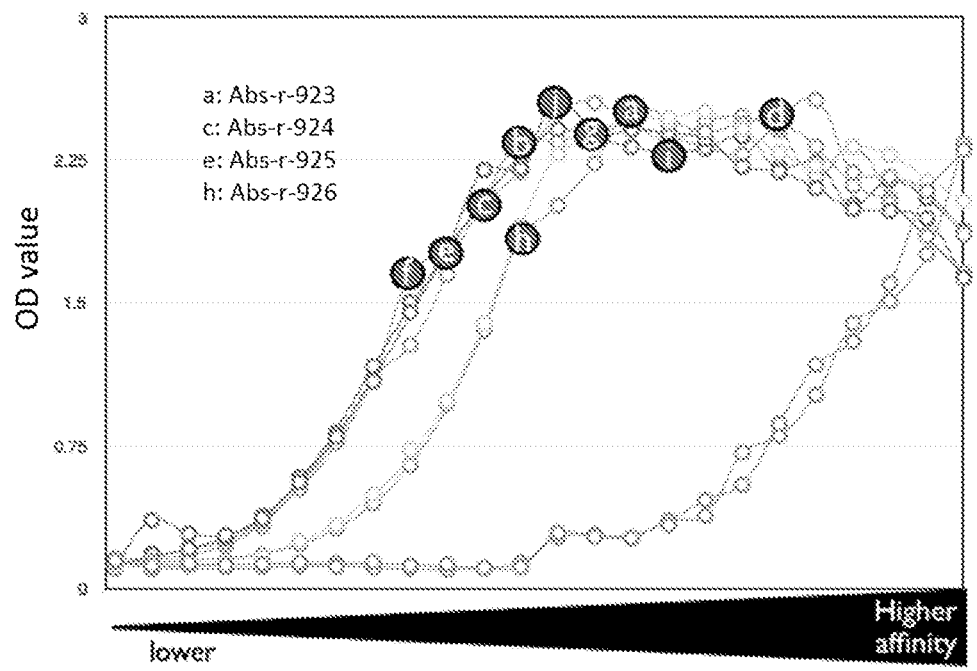
FIG. 1C shows summarizing data on binding specificity of selected rabbit anti-human-PD-1 recombinant antibodies, Abs-r-923, Abs-r-924, Abs-r-925 and Abs-r-926 by ELISA. It is further demonstrated in Examples 1 and 3 of present invention.
Figure 1D:
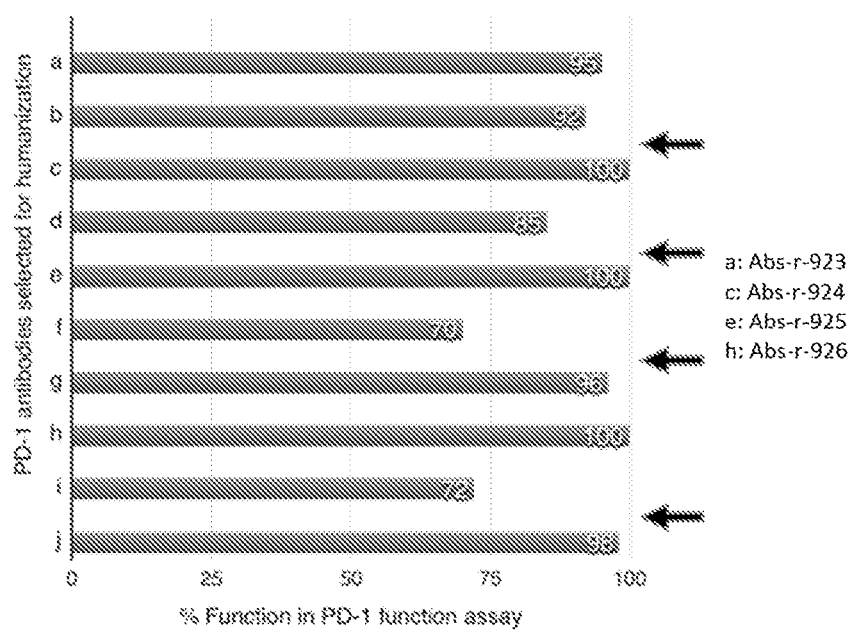
FIG. 1D shows summarizing data on inhibition activity of selected ten rabbit anti-human-PD-1 recombinant antibodies and picked four of them for humanization, Abs-r-923, Abs-r-924, Abs-r-925 and Abs-r-926. It is further demonstrated in Examples 1 and 3 of present invention.
Figure 2:
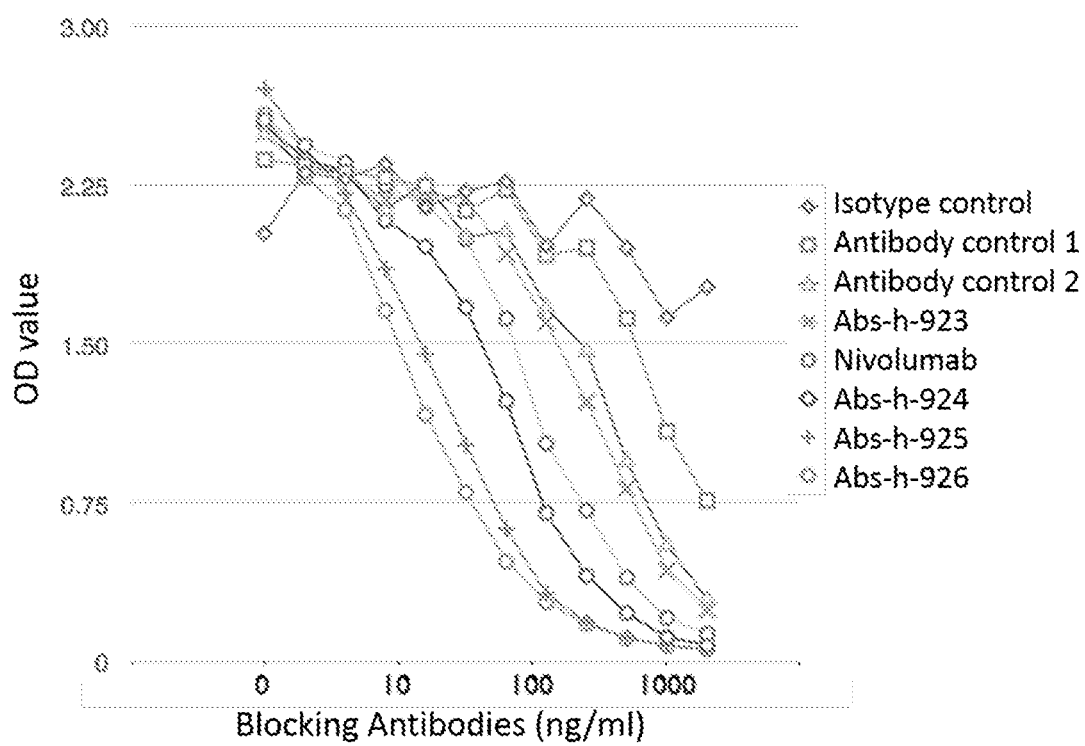
FIG. 2 shows summarizing data on PD-1 binding to PD-L1 inhibited by four humanized anti-human-PD-1 recombinant antibodies, Abs-h-923, Abs-h-924, Abs-h-925 and Abs-h-926. It is further demonstrated in Examples 1 and 3 of present invention.
Figure 7:
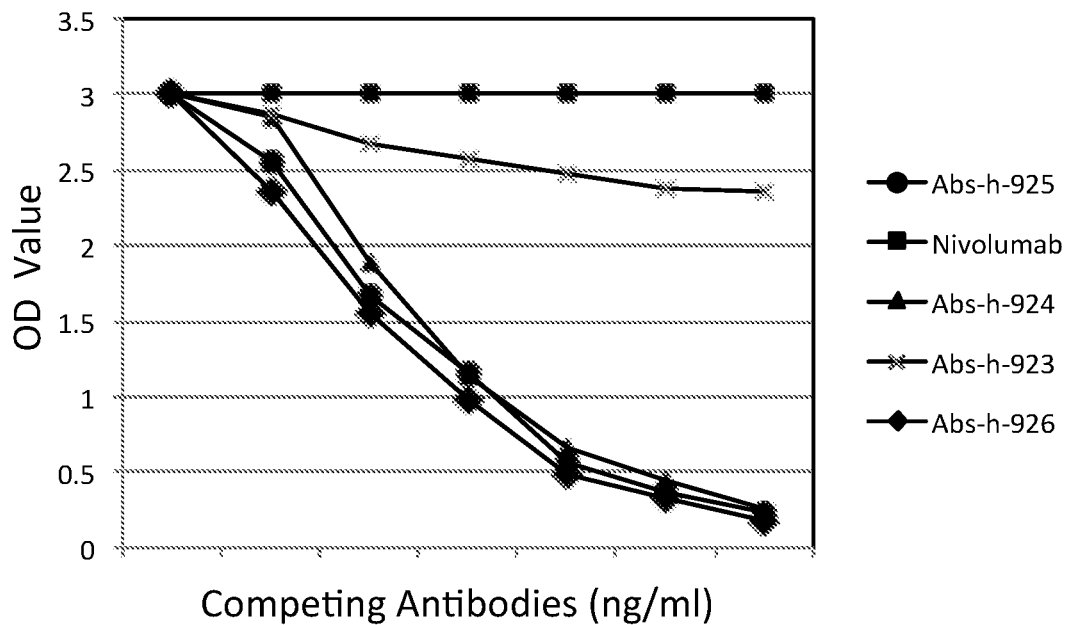
FIG. 7 shows summarizing data on competitive binding to PD-1 of four humanized anti-human-PD-1 recombinant antibodies, Abs-h-923, Abs-h-924, Abs-h-925 and Abs-h-926 with Nivolumab in competition ELISA in Vitro. It is further demonstrated in Example 6 of present invention.
Figure 8:
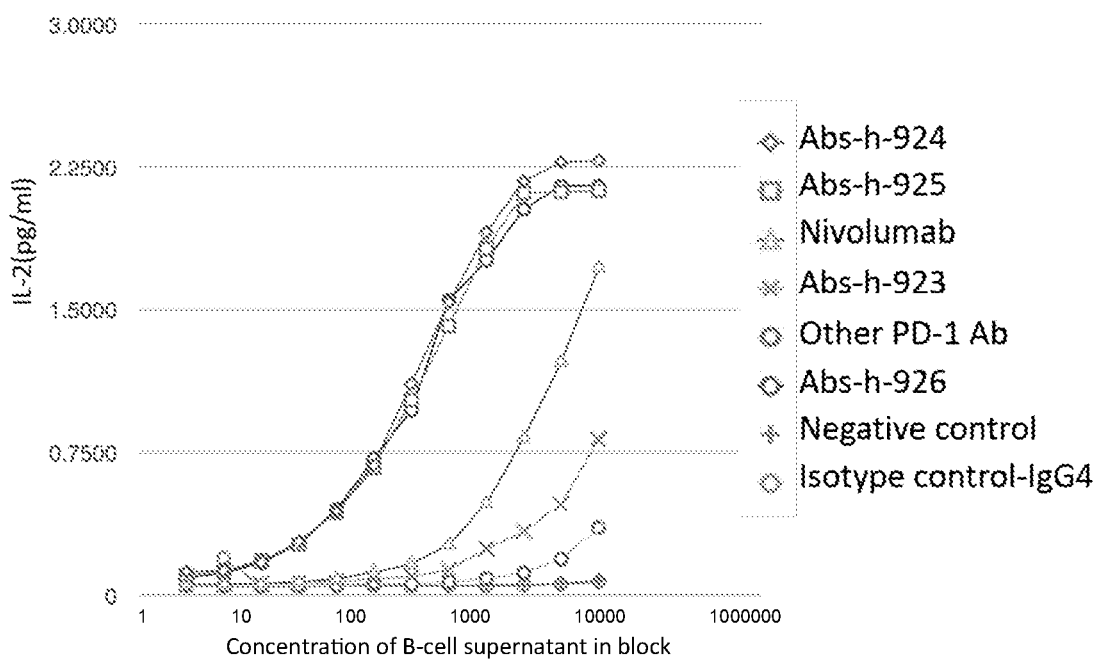
FIG. 8 shows is a bar graph summarizing the results of a mixed lymphocyte reaction (MLR) assay performed on human PBMCs treated with anti-PD-1 antibodies Abs-h-923, Abs-h-924, Abs-h-925 and Abs-h-926. These results indicate that three of four humanized anti-PD-1 antibodies significantly induce increased levels of IL-2 compared to antibody isotype controls (Negative control), two PD-1 antibodies (reference controls) and Nivolumab (Positive control). It is further demonstrated in Example 7 of present invention.

<210> SEQ ID NO 1
<211> LENGTH: 8
<212> TYPE: PRT
<213> ORGANISM: Rabbit

<400> SEQUENCE: 1

Gly Phe Thr Leu Ser Ser Tyr Ala
1               5

<210> SEQ ID NO 2
<211> LENGTH: 8
<212> TYPE: PRT
<213> ORGANISM: Rabbit

<400> SEQUENCE: 2

Ser Asn Ala Gly Asn Gly Asn Thr
1               5

```
<210> SEQ ID NO 3
<211> LENGTH: 6
<212> TYPE: PRT
<213> ORGANISM: Rabbit

<400> SEQUENCE: 3

Tyr Trp Tyr Phe Asp Leu
1               5

<210> SEQ ID NO 4
<211> LENGTH: 8
<212> TYPE: PRT
<213> ORGANISM: Rabbit

<400> SEQUENCE: 4

Gly Phe Ser Ile Ser Ser Tyr Gly
1               5

<210> SEQ ID NO 5
<211> LENGTH: 8
<212> TYPE: PRT
<213> ORGANISM: Rabbit

<400> SEQUENCE: 5

Ile Ser Tyr Asp Gly Ser Asn Lys
1               5

<210> SEQ ID NO 6
<211> LENGTH: 9
<212> TYPE: PRT
<213> ORGANISM: Rabbit

<400> SEQUENCE: 6

Tyr Tyr Tyr Tyr Tyr Gly Met Asp Val
1               5

<210> SEQ ID NO 7
<211> LENGTH: 8
<212> TYPE: PRT
<213> ORGANISM: Rabbit

<400> SEQUENCE: 7

Gly Phe Thr Leu Ser Ser Tyr Ala
1               5

<210> SEQ ID NO 8
<211> LENGTH: 8
<212> TYPE: PRT
<213> ORGANISM: Rabbit

<400> SEQUENCE: 8

Ile Ser Tyr Asp Gly Ser Asn Lys
1               5

<210> SEQ ID NO 9
<211> LENGTH: 9
<212> TYPE: PRT
<213> ORGANISM: Rabbit

<400> SEQUENCE: 9

Tyr Tyr Tyr Tyr Tyr Tyr Met Asp Val
1               5
```

-continued

```
<210> SEQ ID NO 10
<211> LENGTH: 8
<212> TYPE: PRT
<213> ORGANISM: Rabbit

<400> SEQUENCE: 10

Gly Ile Ser Leu Ser Ser Tyr Tyr
1               5

<210> SEQ ID NO 11
<211> LENGTH: 8
<212> TYPE: PRT
<213> ORGANISM: Rabbit

<400> SEQUENCE: 11

Ile Tyr Tyr Ser Gly Ser Thr Asn
1               5

<210> SEQ ID NO 12
<211> LENGTH: 5
<212> TYPE: PRT
<213> ORGANISM: Rabbit

<400> SEQUENCE: 12

Trp Tyr Phe Asp Leu
1               5

<210> SEQ ID NO 13
<211> LENGTH: 6
<212> TYPE: PRT
<213> ORGANISM: Rabbit

<400> SEQUENCE: 13

Gln Ser Gly Ser Ser Phe
1               5

<210> SEQ ID NO 14
<211> LENGTH: 6
<212> TYPE: PRT
<213> ORGANISM: Rabbit

<400> SEQUENCE: 14

Ala Asn Asn Lys Arg Glu
1               5

<210> SEQ ID NO 15
<211> LENGTH: 9
<212> TYPE: PRT
<213> ORGANISM: Rabbit

<400> SEQUENCE: 15

Gly Thr Tyr Thr Asp Ser Pro Pro Thr
1               5

<210> SEQ ID NO 16
<211> LENGTH: 6
<212> TYPE: PRT
<213> ORGANISM: Rabbit

<400> SEQUENCE: 16

Gln Ser Leu Ser Ser Tyr
1               5
```

```
<210> SEQ ID NO 17
<211> LENGTH: 6
<212> TYPE: PRT
<213> ORGANISM: Rabbit

<400> SEQUENCE: 17

Asp Val Ser Asn Arg Ala
1               5

<210> SEQ ID NO 18
<211> LENGTH: 9
<212> TYPE: PRT
<213> ORGANISM: Rabbit

<400> SEQUENCE: 18

Gln Gln Arg Thr Asn Trp Pro Arg Ala
1               5

<210> SEQ ID NO 19
<211> LENGTH: 6
<212> TYPE: PRT
<213> ORGANISM: Rabbit

<400> SEQUENCE: 19

Gln Ser Val Ser Ser Tyr
1               5

<210> SEQ ID NO 20
<211> LENGTH: 6
<212> TYPE: PRT
<213> ORGANISM: Rabbit

<400> SEQUENCE: 20

Glu Ala Ser Asn Arg Ala
1               5

<210> SEQ ID NO 21
<211> LENGTH: 9
<212> TYPE: PRT
<213> ORGANISM: Rabbit

<400> SEQUENCE: 21

Gln Gln Arg Thr Asn Trp Pro Pro Ala
1               5

<210> SEQ ID NO 22
<211> LENGTH: 6
<212> TYPE: PRT
<213> ORGANISM: Rabbit

<400> SEQUENCE: 22

Asn Ser Val Ser Ser Ser
1               5

<210> SEQ ID NO 23
<211> LENGTH: 6
<212> TYPE: PRT
<213> ORGANISM: Rabbit

<400> SEQUENCE: 23

Asp Thr Ser Asn Arg Glu
1               5
```

```
<210> SEQ ID NO 24
<211> LENGTH: 9
<212> TYPE: PRT
<213> ORGANISM: Rabbit

<400> SEQUENCE: 24

Gln Gln Arg Asp Asn Trp Pro Arg Ala
1               5

<210> SEQ ID NO 25
<211> LENGTH: 8
<212> TYPE: PRT
<213> ORGANISM: human

<400> SEQUENCE: 25

Gly Tyr Thr Phe Thr Ser Tyr Ala
1               5

<210> SEQ ID NO 26
<211> LENGTH: 8
<212> TYPE: PRT
<213> ORGANISM: human

<400> SEQUENCE: 26

Ser Asn Ala Gly Asn Gly Asn Thr
1               5

<210> SEQ ID NO 27
<211> LENGTH: 6
<212> TYPE: PRT
<213> ORGANISM: human

<400> SEQUENCE: 27

Tyr Trp Tyr Phe Asp Leu
1               5

<210> SEQ ID NO 28
<211> LENGTH: 8
<212> TYPE: PRT
<213> ORGANISM: human

<400> SEQUENCE: 28

Gly Phe Thr Phe Ser Ser Tyr Gly
1               5

<210> SEQ ID NO 29
<211> LENGTH: 8
<212> TYPE: PRT
<213> ORGANISM: human

<400> SEQUENCE: 29

Ile Ser Tyr Asp Gly Ser Asn Lys
1               5

<210> SEQ ID NO 30
<211> LENGTH: 9
<212> TYPE: PRT
<213> ORGANISM: human

<400> SEQUENCE: 30

Tyr Tyr Tyr Tyr Tyr Gly Met Asp Val
1               5
```

```
<210> SEQ ID NO 31
<211> LENGTH: 8
<212> TYPE: PRT
<213> ORGANISM: human

<400> SEQUENCE: 31

Ala Phe Thr Phe Ser Ser Tyr Ala
1               5

<210> SEQ ID NO 32
<211> LENGTH: 8
<212> TYPE: PRT
<213> ORGANISM: human

<400> SEQUENCE: 32

Ile Ser Tyr Asp Gly Ser Asn Lys
1               5

<210> SEQ ID NO 33
<211> LENGTH: 9
<212> TYPE: PRT
<213> ORGANISM: human

<400> SEQUENCE: 33

Tyr Tyr Tyr Tyr Tyr Tyr Met Asp Val
1               5

<210> SEQ ID NO 34
<211> LENGTH: 8
<212> TYPE: PRT
<213> ORGANISM: human

<400> SEQUENCE: 34

Gly Gly Ser Ile Ser Ser Tyr Tyr
1               5

<210> SEQ ID NO 35
<211> LENGTH: 8
<212> TYPE: PRT
<213> ORGANISM: human

<400> SEQUENCE: 35

Ile Tyr Tyr Ser Gly Ser Thr Asn
1               5

<210> SEQ ID NO 36
<211> LENGTH: 5
<212> TYPE: PRT
<213> ORGANISM: human

<400> SEQUENCE: 36

Trp Tyr Phe Asp Leu
1               5

<210> SEQ ID NO 37
<211> LENGTH: 6
<212> TYPE: PRT
<213> ORGANISM: human

<400> SEQUENCE: 37

Gln Ser Gly Ser Ser Phe
1               5
```

```
<210> SEQ ID NO 38
<211> LENGTH: 6
<212> TYPE: PRT
<213> ORGANISM: human

<400> SEQUENCE: 38

Ala Asn Asn Lys Arg Glu
1               5

<210> SEQ ID NO 39
<211> LENGTH: 9
<212> TYPE: PRT
<213> ORGANISM: human

<400> SEQUENCE: 39

Gly Thr Tyr Thr Asp Ser Pro Pro Thr
1               5

<210> SEQ ID NO 40
<211> LENGTH: 6
<212> TYPE: PRT
<213> ORGANISM: human

<400> SEQUENCE: 40

Gln Ser Leu Ser Ser Tyr
1               5

<210> SEQ ID NO 41
<211> LENGTH: 6
<212> TYPE: PRT
<213> ORGANISM: human

<400> SEQUENCE: 41

Asp Val Ser Asn Arg Ala
1               5

<210> SEQ ID NO 42
<211> LENGTH: 9
<212> TYPE: PRT
<213> ORGANISM: human

<400> SEQUENCE: 42

Gln Gln Arg Thr Asn Trp Pro Arg Ala
1               5

<210> SEQ ID NO 43
<211> LENGTH: 6
<212> TYPE: PRT
<213> ORGANISM: human

<400> SEQUENCE: 43

Gln Ser Val Ser Ser Tyr
1               5

<210> SEQ ID NO 44
<211> LENGTH: 6
<212> TYPE: PRT
<213> ORGANISM: human

<400> SEQUENCE: 44

Glu Ala Ser Asn Arg Ala
1               5
```

```
<210> SEQ ID NO 45
<211> LENGTH: 9
<212> TYPE: PRT
<213> ORGANISM: human

<400> SEQUENCE: 45

Gln Gln Arg Thr Asn Trp Pro Pro Ala
1               5

<210> SEQ ID NO 46
<211> LENGTH: 6
<212> TYPE: PRT
<213> ORGANISM: human

<400> SEQUENCE: 46

Asn Ser Val Ser Ser Ser
1               5

<210> SEQ ID NO 47
<211> LENGTH: 6
<212> TYPE: PRT
<213> ORGANISM: human

<400> SEQUENCE: 47

Asp Thr Ser Asn Arg Glu
1               5

<210> SEQ ID NO 48
<211> LENGTH: 9
<212> TYPE: PRT
<213> ORGANISM: human

<400> SEQUENCE: 48

Gln Gln Arg Asp Asn Trp Pro Arg Ala
1               5

<210> SEQ ID NO 49
<211> LENGTH: 345
<212> TYPE: DNA
<213> ORGANISM: Rabbit

<400> SEQUENCE: 49
tgccagagcg tggaagaaag cgaaggcggc ctggtgaaac cgggcgcgag cctgaccctg      60
agctgcaccg cgagcggctt taccctgagc agctatgcga tgcattgggt gcgccaggcg     120
ccgggcaacg gcctggaatg gattggctgg agcaacgcgg gcaacggcaa caccaaatat     180
agccaggaat tcagggccg ctttaccatt acccgcaaca ccagcctgag caccgtgacc     240
ctggaaatga ccagcctgac cgcggcggat accgcgacct attttgcgc gcgctattgg     300 tattttgatc tgtggggccc gggcaccctg gtgaccgtga gcagc                    345

<210> SEQ ID NO 50
<211> LENGTH: 115
<212> TYPE: PRT
<213> ORGANISM: Rabbit

<400> SEQUENCE: 50

Cys Gln Ser Val Glu Glu Ser Glu Gly Gly Leu Val Lys Pro Gly Ala
1               5                   10                  15

Ser Leu Thr Leu Ser Cys Thr Ala Ser Gly Phe Thr Leu Ser Ser Tyr
            20                  25                  30

Ala Met His Trp Val Arg Gln Ala Pro Gly Asn Gly Leu Glu Trp Ile
        35                  40                  45
```

Gly Trp Ser Asn Ala Gly Asn Gly Asn Thr Lys Tyr Ser Gln Glu Phe
    50                  55                  60

Gln Gly Arg Phe Thr Ile Thr Arg Asn Thr Ser Leu Ser Thr Val Thr
65                  70                  75                  80

Leu Glu Met Thr Ser Leu Thr Ala Ala Asp Thr Ala Thr Tyr Phe Cys
                85                  90                  95

Ala Arg Tyr Trp Tyr Phe Asp Leu Trp Gly Pro Gly Thr Leu Val Thr
                100                 105                 110

Val Ser Ser
        115

<210> SEQ ID NO 51
<211> LENGTH: 330
<212> TYPE: DNA
<213> ORGANISM: Rabbit

<400> SEQUENCE: 51
gaactggtgc tgacccagac cccgagcagc gtgagcgcgg cggtgggcgg caccgtgacc    60
attaactgcc aggcgagcca gagcggcagc agctttgtgg cgtggtatca gcagaaaccg   120
ggccagccgc cgaaactgct gatttatgcg aacaacaaac gcgaaaccgg cgtgccgagc   180
cgctttagcg gcagcggcag cggcaccgat tttaccctga ccattagcag cctggaatgc   240
gaagatgcgg cgacctatta ttgcggcacc tataccgata gcccgccgac ctttggcggc   300
ggcaccaaag tggtggtgaa aggcgatccg                                    330

<210> SEQ ID NO 52
<211> LENGTH: 110
<212> TYPE: PRT
<213> ORGANISM: Rabbit

<400> SEQUENCE: 52

Glu Leu Val Leu Thr Gln Thr Pro Ser Ser Val Ser Ala Ala Val Gly
1               5                   10                  15

Gly Thr Val Thr Ile Asn Cys Gln Ala Ser Gln Ser Gly Ser Ser Phe
                20                  25                  30

Val Ala Trp Tyr Gln Gln Lys Pro Gly Gln Pro Pro Lys Leu Leu Ile
            35                  40                  45

Tyr Ala Asn Asn Lys Arg Glu Thr Gly Val Pro Ser Arg Phe Ser Gly
    50                  55                  60

Ser Gly Ser Gly Thr Asp Phe Thr Leu Thr Ile Ser Ser Leu Glu Cys
65                  70                  75                  80

Glu Asp Ala Ala Thr Tyr Tyr Cys Gly Thr Tyr Thr Asp Ser Pro Pro
                85                  90                  95

Thr Phe Gly Gly Gly Thr Lys Val Val Val Lys Gly Asp Pro
                100                 105                 110

<210> SEQ ID NO 53
<211> LENGTH: 354
<212> TYPE: DNA
<213> ORGANISM: Rabbit

<400> SEQUENCE: 53
caggaaagcg tgaaagaaag cggcggcggc ctggtgaaac cgggcgatac cctgaccctg    60
acctgcaaag tgagcggctt tagcattagc agctatggca tgcattgggt cgccaggcg    120 ccgggcaaag cctggaatg gattggcgtg attagctatg atggcagcaa caaatattat   180
gcggatagcg tgaaaggccg ctttaccatt agccgcaaca ccaaccagaa caccgtgacc   240

```
ctgaaaatga ccagcctgac cgcggatgat accgcgacct attttttgcgc gcgctattat    300 tattattatg gcatggatgt gtggggccag ggcaccctgg tgaccgtgag cagc           354
```

<210> SEQ ID NO 54
<211> LENGTH: 118
<212> TYPE: PRT
<213> ORGANISM: Rabbit

<400> SEQUENCE: 54

```
Gln Glu Ser Val Lys Glu Ser Gly Gly Gly Leu Val Lys Pro Gly Asp
1               5                   10                  15

Thr Leu Thr Leu Thr Cys Lys Val Ser Gly Phe Ser Ile Ser Ser Tyr
            20                  25                  30

Gly Met His Trp Val Arg Gln Ala Pro Gly Lys Gly Leu Glu Trp Ile
        35                  40                  45

Gly Val Ile Ser Tyr Asp Gly Ser Asn Lys Tyr Tyr Ala Asp Ser Val
    50                  55                  60

Lys Gly Arg Phe Thr Ile Ser Arg Asn Thr Asn Gln Asn Thr Val Thr
65                  70                  75                  80

Leu Lys Met Thr Ser Leu Thr Ala Asp Asp Thr Ala Thr Tyr Phe Cys
                85                  90                  95

Ala Arg Tyr Tyr Tyr Tyr Tyr Gly Met Asp Val Trp Gly Gln Gly Thr
            100                 105                 110

Leu Val Thr Val Ser Ser
        115
```

<210> SEQ ID NO 55
<211> LENGTH: 330
<212> TYPE: DNA
<213> ORGANISM: Rabbit

<400> SEQUENCE: 55

```
gaaattgtgc tgacccagac cccgagcagc gtgagcgcgg cggtgggcag caccgtgacc    60
attaactgcc gcggcagcca gagcctgagc agctatctgg cgtggtatca gcagaaaccg   120
ggccagcgcc cgaaactgct gatttatgat gtgagcaacc gcgcgaccgg cgtgccgcgc   180
cgctttaaag gcagcggcag cggcacccag tttaccctga ccattagcgg cgtgcaggcg   240
gatgatgcgg cgacctatta ttgccagcag cgcaccaact ggccgcgcgc gtttggcggc   300
ggcaccaaag tggatgtgaa aggcgatccg                                    330
```

<210> SEQ ID NO 56
<211> LENGTH: 110
<212> TYPE: PRT
<213> ORGANISM: Rabbit

<400> SEQUENCE: 56

```
Glu Ile Val Leu Thr Gln Thr Pro Ser Ser Val Ser Ala Ala Val Gly
1               5                   10                  15

Ser Thr Val Thr Ile Asn Cys Arg Gly Ser Gln Ser Leu Ser Ser Tyr
            20                  25                  30

Leu Ala Trp Tyr Gln Gln Lys Pro Gly Gln Arg Pro Lys Leu Leu Ile
        35                  40                  45

Tyr Asp Val Ser Asn Arg Ala Thr Gly Val Pro Arg Arg Phe Lys Gly
    50                  55                  60

Ser Gly Ser Gly Thr Gln Phe Thr Leu Thr Ile Ser Gly Val Gln Ala
65                  70                  75                  80
```

Asp Asp Ala Ala Thr Tyr Tyr Cys Gln Gln Arg Thr Asn Trp Pro Arg
            85                  90                  95

Ala Phe Gly Gly Gly Thr Lys Val Asp Val Lys Gly Asp Pro
            100                 105                 110

<210> SEQ ID NO 57
<211> LENGTH: 345
<212> TYPE: DNA
<213> ORGANISM: Rabbit

<400> SEQUENCE: 57
tgccagagcc tggaagaaag cggcggcggc ctggtgcagc cgggcaccac cctgaccctg      60
agctgcaccg tgagcggctt taccctgagc agctatgcga tgatgtgggt gcgccaggcg     120
ccgggcaaag gcctggaatg gattggcgtg attagctatg atggcagcaa caaatattat     180
gcgcagagcg tgaaaggccg ctttaccatt agccgcaaca ccagccagaa caccgtgacc     240
ctgaaaatga ccagcctgac cgcggaagat accgcgacct attttgcgc gcgctattat     300 tattattatt atatggatgt gtggggcccg gtgaccgtga gcagc                     345

<210> SEQ ID NO 58
<211> LENGTH: 115
<212> TYPE: PRT
<213> ORGANISM: Rabbit

<400> SEQUENCE: 58

Cys Gln Ser Leu Glu Glu Ser Gly Gly Gly Leu Val Gln Pro Gly Thr
1               5                   10                  15

Thr Leu Thr Leu Ser Cys Thr Val Ser Gly Phe Thr Leu Ser Ser Tyr
            20                  25                  30

Ala Met Met Trp Val Arg Gln Ala Pro Gly Lys Gly Leu Glu Trp Ile
        35                  40                  45

Gly Val Ile Ser Tyr Asp Gly Ser Asn Lys Tyr Tyr Ala Gln Ser Val
    50                  55                  60

Lys Gly Arg Phe Thr Ile Ser Arg Asn Thr Ser Gln Asn Thr Val Thr
65                  70                  75                  80

Leu Lys Met Thr Ser Leu Thr Ala Glu Asp Thr Ala Thr Tyr Phe Cys
            85                  90                  95

Ala Arg Tyr Tyr Tyr Tyr Tyr Tyr Met Asp Val Trp Gly Pro Val Thr
            100                 105                 110

Val Ser Ser
        115

<210> SEQ ID NO 59
<211> LENGTH: 333
<212> TYPE: DNA
<213> ORGANISM: Rabbit

<400> SEQUENCE: 59
gaactggtgc tgacccagac cccgagcagc gtgagcgcgg cggtgggcgg caccgtgacc      60
acaattacct gccgcgcgag ccagagcgtg agcagctatc tggcgtggta tcagcagaaa     120
ccgggccagg cgccgaaact gctgatttat gaagcgagca ccgcgcgac cggcgtgccg      180 agccgcttta gcggcagcgg cagcggcacc gaatttaccc tgaccattag cggcgtgcag     240
tgcgatgatg cagcgaccta ttattgccag cagcgcacca ctggccgcc ggcgtttggc     300 ggcggcacca aagtggtggt gaaaggcgat ccg                                  333

<210> SEQ ID NO 60
<211> LENGTH: 110
<212> TYPE: PRT
<213> ORGANISM: Rabbit

<400> SEQUENCE: 60

Glu Leu Val Leu Thr Gln Thr Pro Ser Ser Val Ser Ala Ala Val Gly
1               5                   10                  15

Gly Thr Val Thr Ile Thr Cys Arg Ala Ser Gln Ser Val Ser Ser Tyr
            20                  25                  30

Leu Ala Trp Tyr Gln Gln Lys Pro Gly Gln Ala Pro Lys Leu Leu Ile
        35                  40                  45

Tyr Glu Ala Ser Asn Arg Ala Thr Gly Val Pro Ser Arg Phe Ser Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Gln Arg Thr Asn Trp Pro Pro
                85                  90                  95

Ala Phe Gly Gly Gly Thr Lys Val Val Val Lys Gly Asp Pro
            100                 105                 110

<210> SEQ ID NO 61
<211> LENGTH: 342
<212> TYPE: DNA
<213> ORGANISM: Rabbit

<400> SEQUENCE: 61
tgccagagcg tggaagaaag cggcggcggc ctggtgaaac cgaccgatac cctgaccctg      60
acctgcaccg tgagcggcat tagcctgagc agctattatt ggagctgggt gcgccaggcg     120
ccgggcaaag gcctggaatg gattggctat atttattata gcggaggcag caccaactat     180
aacccgagcc tgaaaagccg cagcaccatt agccgcaaca ccaacaccaa caccgtgacc     240
ctgaaaatga ccagcctgac cgcggcggat accgcgacct attattgcgc gcgctggtat     300
tttgatctgt ggggccaggg cacccctggtg accgtgagca gc                       342

<210> SEQ ID NO 62
<211> LENGTH: 114
<212> TYPE: PRT
<213> ORGANISM: Rabbit

<400> SEQUENCE: 62

Cys Gln Ser Val Glu Glu Ser Gly Gly Gly Leu Val Lys Pro Thr Asp
1               5                   10                  15

Thr Leu Thr Leu Thr Cys Thr Val Ser Gly Ile Ser Leu Ser Ser Tyr
            20                  25                  30

Tyr Trp Ser Trp Val Arg Gln Ala Pro Gly Lys Gly Leu Glu Trp Ile
        35                  40                  45

Gly Tyr Ile Tyr Tyr Ser Gly Gly Thr Asn Tyr Asn Pro Ser Leu
    50                  55                  60

Lys Ser Arg Ser Thr Ile Ser Arg Asn Thr Asn Thr Asn Thr Val Thr
65                  70                  75                  80

Leu Lys Met Thr Ser Leu Thr Ala Ala Asp Thr Ala Thr Tyr Tyr Cys
                85                  90                  95

Ala Arg Trp Tyr Phe Asp Leu Trp Gly Gln Gly Thr Leu Val Thr Val
            100                 105                 110

Ser Ser

<210> SEQ ID NO 63
<211> LENGTH: 330
<212> TYPE: DNA
<213> ORGANISM: Rabbit

<400> SEQUENCE: 63

| | | | | | |
|---|---|---|---|---|---|
| gaaattgtgc | tgacccagag | cccgagcagc | gtgagcgtga | gcgtgggcag | caccgtgacc | 60 |
| attaactgcc | gcgcgagcaa | cagcgtgagc | agcagcctgg | cgtggtatca | gcagaaaccg | 120 |
| ggccaggcgc | cgcgcctgct | gatttatgat | accagcaacc | gcgaaaccgg | cgtgccgagc | 180 |
| cgctttagcg | gcagccgcag | cggcaccgaa | tttaccctga | ccattagcgg | cgtgcagtgc | 240 |
| gcggatgcgg | cgacctatta | ttgccagcag | cgcgataact | ggccgcgcgc | gtttggcggc | 300 |
| ggcaccaaag | tggtggtgaa | acgcgatgtg | | | | 330 |

<210> SEQ ID NO 64
<211> LENGTH: 110
<212> TYPE: PRT
<213> ORGANISM: Rabbit

<400> SEQUENCE: 64

Glu Ile Val Leu Thr Gln Ser Pro Ser Ser Val Ser Val Ser Val Gly
1               5                   10                  15

Ser Thr Val Thr Ile Asn Cys Arg Ala Ser Asn Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Thr Ser Asn Arg Glu Thr Gly Val Pro Ser Arg Phe Ser Gly
    50                  55                  60

Ser Arg Ser Gly Thr Glu Phe Thr Leu Thr Ile Ser Gly Val Gln Cys
65                  70                  75                  80

Ala Asp Ala Ala Thr Tyr Tyr Cys Gln Gln Arg Asp Asn Trp Pro Arg
                85                  90                  95

Ala Phe Gly Gly Gly Thr Lys Val Val Val Lys Arg Asp Val
            100                 105                 110

<210> SEQ ID NO 65
<211> LENGTH: 345
<212> TYPE: DNA
<213> ORGANISM: human

<400> SEQUENCE: 65

| | | | | | |
|---|---|---|---|---|---|
| caggtgcagc | tggtgcagag | cggcgcggaa | gtgaaaaaac | cgggcgcgag | cgtgaaagtg | 60 |
| agctgcaaag | cgagcggcta | tacctttacc | agctatgcga | tgcattgggt | gcgccaggcg | 120 |
| ccgggccagc | gcctggaatg | gatgggctgg | agcaacgcgg | gcaacggcaa | caccaaatat | 180 |
| agccaggaat | tcagggccg | cgtgaccatt | acccgcgata | ccagcgcgag | caccgcgtat | 240 |
| atggaactga | gcagcctgcg | cagcgaagat | atggcggtgt | attattgcgc | gcgctattgg | 300 |
| tattttgatc | tgtggggccg | cggcaccctg | gtgaccgtga | gcagc | | 345 |

<210> SEQ ID NO 66
<211> LENGTH: 115
<212> TYPE: PRT
<213> ORGANISM: human

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ser Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Tyr Trp Tyr Phe Asp Leu Trp Gly Arg Gly Thr Leu Val Thr
            100                 105                 110

Val Ser Ser
        115

<210> SEQ ID NO 67
<211> LENGTH: 330
<212> TYPE: DNA
<213> ORGANISM: human

<400> SEQUENCE: 67
gagatcgccc tgacccagag ccccgctaca ctgagtctga gccctggcga gcgcgcaaca        60
ctgagttgcc gggccagcca gagcggctct agcttcgtgg cctggtatca gcagaaacca       120
ggccaagccc cccggctcct gatctatgcc aacaacaaga gagagactgg catccctgcc       180
cggttctccg gatcaggttc cgggaccgac tttacccttac tatctcctc tctggaacca       240 gaagactttg ctgtgtacta ctgcggcacc tacacagatt caccccccac gttcggacag       300
gggaccaagg tggagattaa gaggaccgtg                                         330

<210> SEQ ID NO 68
<211> LENGTH: 110
<212> TYPE: PRT
<213> ORGANISM: human

<400> SEQUENCE: 68

Glu Ile Ala Leu Thr Gln Ser Pro Ala Thr Leu Ser Leu Ser Pro Gly
1               5                   10                  15

Glu Arg Ala Thr Leu Ser Cys Arg Ala Ser Gln Ser Gly Ser Ser Phe
            20                  25                  30

Val Ala Trp Tyr Gln Gln Lys Pro Gly Gln Ala Pro Arg Leu Leu Ile
        35                  40                  45

Tyr Ala Asn Asn Lys Arg Glu Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Thr Tyr Thr Asp Ser Pro Pro
                85                  90                  95

Thr Phe Gly Gln Gly Thr Lys Val Glu Ile Lys Arg Thr Val
            100                 105                 110

<210> SEQ ID NO 69
<211> LENGTH: 354
<212> TYPE: DNA
<213> ORGANISM: human

<400> SEQUENCE: 69

```
caggtgcagc tggtggaaag cggcggcggc gtggtgcagc cgggccgcag cctgcgcctg      60
agctgcgcgg cgagcggctt tacctttagc agctatggca tgcattgggt gcgccaggcg     120
ccgggcaaag cctggaatgg gtggcggtg attagctatg atggcagcaa caaatattat     180
gcggatagcg tgaaaggccg ctttaccatt agccgcgata acagcaaaaa caccctgtat     240
ctgcagatga acagcctgcg cgcggaagat accgcggtgt attattgcgc gcgctattat     300
tattattatg gcatggatgt gtggggccag ggcaccaccg tgaccgtgag cagc            354
```

<210> SEQ ID NO 70
<211> LENGTH: 118
<212> TYPE: PRT
<213> ORGANISM: human

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser
        115

<210> SEQ ID NO 71
<211> LENGTH: 330
<212> TYPE: DNA
<213> ORGANISM: human

<400> SEQUENCE: 71

```
gagattgtcc tgactcagtc tcccgctacc ctttccttgt ctccaggcga acgggccacc      60
attagctgcc gcggaagcca gagcctgtcc tcatacctcg cttggtatca acagcggcct     120
ggacaggcac ccaggctgct gatctacgac gtgagcaacc gggccacagg gatccccgcc     180
cggtttagtg ggagcggtag cggcacagat ttcactctga ccatcagcgg cctggaaccc     240
gaggacttcg ccgtgtacta ttgccagcag cggaccaact ggcccagagc cttcggccaa     300
ggcacgaagg tggagatcaa gcggaccgtg                                       330
```

<210> SEQ ID NO 72
<211> LENGTH: 110
<212> TYPE: PRT
<213> ORGANISM: human

-continued

<400> SEQUENCE: 72

Glu Ile Val Leu Thr Gln Ser Pro Ala Thr Leu Ser Leu Ser Pro Gly
1               5                   10                  15

Glu Arg Ala Thr Ile Ser Cys Arg Gly Ser Gln Ser Leu Ser Ser Tyr
            20                  25                  30

Leu Ala Trp Tyr Gln Gln Arg Pro Gly Gln Ala Pro Arg Leu Leu Ile
        35                  40                  45

Tyr Asp Val Ser Asn Arg Ala Thr Gly Ile Pro Ala Arg Phe Ser Gly
50                  55                  60

Ser Gly Ser Gly Thr Asp Phe Thr Leu Thr Ile Ser Gly Leu Glu Pro
65                  70                  75                  80

Glu Asp Phe Ala Val Tyr Tyr Cys Gln Gln Arg Thr Asn Trp Pro Arg
                85                  90                  95

Ala Phe Gly Gln Gly Thr Lys Val Glu Ile Lys Arg Thr Val
            100                 105                 110

<210> SEQ ID NO 73
<211> LENGTH: 354
<212> TYPE: DNA
<213> ORGANISM: human

<400> SEQUENCE: 73
caggtgcagc tggtggatag cggcggcggc gtggtgcagc cgggccgcag cctgcgcctg      60
agctgcgcgg cgagcgcgtt tacctttagc agctatgcga tgcattgggt gcgccaggcg     120
ccgggcaaag gcctggaatg gtggcggtg attagctatg atggcagcaa caaatattat      180
gcggatagcg tgaaaggccg ctttaccatt agccgcgata acagcaaaaa caccctgtat     240
ctgcagatga acagcctgcg cgcggaagat accgcggtgt attattgcgc gcgctattat     300
tattattatt atatggatgt gtggggcaaa ggcaccaccg tgaccgtgag cagc            354

<210> SEQ ID NO 74
<211> LENGTH: 118
<212> TYPE: PRT
<213> ORGANISM: human

<400> SEQUENCE: 74

Gln Val Gln Leu Val Asp Ser Gly Gly Gly Val Val Gln Pro Gly Arg
1               5                   10                  15

Ser Leu Arg Leu Ser Cys Ala Ala Ser Ala Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Tyr Tyr Met Asp Val Trp Gly Lys Gly Thr
            100                 105                 110

Thr Val Thr Val Ser Ser
            115

<210> SEQ ID NO 75
<211> LENGTH: 330
<212> TYPE: DNA
<213> ORGANISM: human

<400> SEQUENCE: 75

```
gagatcgtgc tgacgcaatc acccgccacc ctgagcctgt cccctggcga gcgggctaca      60
ctgagctgcc gggccagtca gtcagtgagc agttacttgg cttggtacca gcagaaaccc     120
ggccaagccc cacggctgct tatttatgag gcatccaaca gagcgaccgg catccctgcc     180
cgcttctctg gctctggatc cgggaccgac ttcactctca ctatcagcag cctggaaccc     240
gaggacttcg cagtctatta ctgccagcag aggaccaact ggccccccagc ctttggtcag     300 ggcacaaagg tggaaatcaa gcggaccgtg                                       330
```

<210> SEQ ID NO 76
<211> LENGTH: 110
<212> TYPE: PRT
<213> ORGANISM: human

<400> SEQUENCE: 76

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Glu Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Pro
                85                  90                  95

Ala Phe Gly Gln Gly Thr Lys Val Glu Ile Lys Arg Thr Val
            100                 105                 110
```

<210> SEQ ID NO 77
<211> LENGTH: 339
<212> TYPE: DNA
<213> ORGANISM: human

<400> SEQUENCE: 77

```
caggtgcagc tgcaggaaag cggcccgggc ctggtgaaac cgagcgaaac cctgagcctg      60
acctgcaccg tgagcggcgg cagcattagc agctattatt ggagctggat tcgccagccg     120
ccgggcaaag gcctggaatg gattggctat atttattata gcggcagcac caactataac     180
ccgagcctga aaagccgcgt gaccattagc gtggatacca gcaaaaacca gtttagcctg     240
aaactgagca gcgtgaccgc ggcggatacc gcggtgtatt attgcgcgta ttggtatttt     300
gatctgtggg gccgcggcac cctggtgacc gtgagcagc                             339
```

<210> SEQ ID NO 78
<211> LENGTH: 114
<212> TYPE: PRT
<213> ORGANISM: human

-continued

<400> SEQUENCE: 78

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Tyr Trp Tyr Phe Asp Leu Trp Gly Arg Gly Thr Leu Val Thr Val
            100                 105                 110

Ser Ser
```

<210> SEQ ID NO 79
<211> LENGTH: 330
<212> TYPE: DNA
<213> ORGANISM: human

<400> SEQUENCE: 79

```
gagattgtgc tgactcagtc cccatccacc ctgagtctgt cacccggaca gaaagccact      60
ctgtcttgca gagccagcaa tagcgtcagc tcaagcctgg cctggtatca gcagaagccc     120
gggaaagctc cccggcttat gatctacgac accagtaacc gggaaaccgg catccctgag     180
cgcttcagcg gctctaagtc tggcacagat ttcagcctca caatcagctc cctggagccc     240
ggtgactttg ccgtgtacta ctgccagcag cgggacaact ggccccgggc attcggccaa     300
ggcacgaagg tgaccatcaa gaggaccgtg                                      330
```

<210> SEQ ID NO 80
<211> LENGTH: 110
<212> TYPE: PRT
<213> ORGANISM: human

<400> SEQUENCE: 80

```
Glu Ile Val Leu Thr Gln Ser Pro Ser Thr Leu Ser Leu Ser Pro Gly
1               5                   10                  15

Gln Lys Ala Thr Leu Ser Cys Arg Ala Ser Asn Ser Val Ser Ser Ser
            20                  25                  30

Leu Ala Trp Tyr Gln Gln Lys Pro Gly Lys Ala Pro Arg Leu Met Ile
        35                  40                  45

Tyr Asp Thr Ser Asn Arg Glu Thr Gly Ile Pro Glu Arg Phe Ser Gly
    50                  55                  60

Ser Lys Ser Gly Thr Asp Phe Ser Leu Thr Ile Ser Ser Leu Glu Pro
65                  70                  75                  80

Gly Asp Phe Ala Val Tyr Tyr Cys Gln Gln Arg Asp Asn Trp Pro Arg
                85                  90                  95

Ala Phe Gly Gln Gly Thr Lys Val Thr Ile Lys Arg Thr Val
            100                 105                 110
```

The invention claimed is:

1. An anti-PD-1 antibody, or antigen binding fragment, which comprises:
   a) a heavy chain variable region (H-CVR) having complementarity determining regions (CDRs) of:
   HCDR1 of SEQ ID NO: 1 or SEQ ID NO: 25; and
   HCDR2 of SEQ ID NO: 2; and
   HCDR3 of SEQ ID NO: 3; and
   a light chain variable region (L-CVR) having CDRs of:
   LCDR1 of SEQ ID NO: 13; and
   LCDR2 of SEQ ID NO: 14; and
   LCDR3 of SEQ ID NO: 15; or
   b) a heavy chain variable region (H-CVR) having CDRs of:
   HCDR1 of SEQ ID NO: 4 or SEQ ID NO: 28; and
   HCDR2 of SEQ ID NO: 5; and
   HCDR3 of SEQ ID NO: 6; and
   a light chain variable region (L-CVR) having CDRs of:
   LCDR1 of SEQ ID NO: 16; and
   LCDR2 of SEQ ID NO: 17; and
   LCDR3 of SEQ ID NO: 18; or
   c) a heavy chain variable region (H-CVR) having CDRs of:
   HCDR1 of SEQ ID NO: 7 or SEQ ID NO: 31; and
   HCDR2 of SEQ ID NO: 8; and
   HCDR3 of SEQ ID NO: 9; and
   a light chain variable region (L-CVR) having CDRs of:
   LCDR1 of SEQ ID NO: 19; and
   LCDR2 of SEQ ID NO: 20; and
   LCDR3 of SEQ ID NO: 21; or
   d) a heavy chain variable region (H-CVR) having CDRs of:
   HCDR1 of SEQ ID NO: 10 or SEQ ID NO: 34; and
   HCDR2 of SEQ ID NO: 11; and
   HCDR3 of SEQ ID NO: 12; and
   a light chain variable region (L-CVR) having CDRs of:
   LCDR1 of SEQ ID NO: 22; and
   LCDR2 of SEQ ID NO: 23; and
   LCDR3 of SEQ ID NO: 24.

2. The anti-PD-1 antibody, or antigen binding fragment, of claim 1 comprising:
   a VH region amino acid sequence comprising SEQ ID NO 66 and a VL region amino acid sequence comprising SEQ ID 68, or
   a VH region amino acid sequence comprising SEQ ID NO 70 and a VL region amino acid sequence comprising SEQ ID NO 72, or
   a VH region amino acid sequence comprising SEQ ID NO 74 and a VL region amino acid sequence comprising SEQ ID NO 76, or
   a VH region amino acid sequence comprising SEQ ID NO 78 and a VL region amino acid sequence comprising SEQ ID NO 80.

3. The anti-PD-1 antibody, or antigen binding fragment, of claim 1, wherein the antibody or antigen binding fragment specifically binds to an epitope within the extracellular domain of human or mouse PD-1.

4. The anti-PD-1 antibody or antigen binding fragment, of claim 1, further comprising a humanized IgG1 or IgG4 heavy chain framework region.

5. The anti-PD-1 antibody, or antigen binding fragment, of claim 1, wherein the antibody or antigen binding fragment competes with Nivolumab for binding to human PD-1.

6. The anti-PD-1 antibody, or antigen binding fragment, of claim 1, wherein the antibody or antigen binding fragment induces IL-2 release in Mixed Lymphocyte Reaction (MLR).

7. A method for treating a cancer or an infectious disease in a subject, which method comprises administration, to a human or animal subject, of the anti-PD-1 antibody according to claim 1, in a therapeutically sufficient dose.

8. The method of claim 7, wherein the anti-PD-1 antibody comprises:
   a VH region amino acid sequence comprising SEQ ID NO 66 and a VL region amino acid sequence comprising SEQ ID 68, or
   a VH region amino acid sequence comprising SEQ ID NO 70 and a VL region amino acid sequence comprising SEQ ID NO 72, or
   a VH region amino acid sequence comprising SEQ ID NO 74 and a VL region amino acid sequence comprising SEQ ID NO 76, or
   a VH region amino acid sequence comprising SEQ ID NO 78 and a VL region amino acid sequence comprising SEQ ID NO 80.

9. The method of claim 7, wherein the anti-PD-1 antibody specifically binds to an epitope within the extracellular domain of human or mouse PD-1.

10. The method of claim 7, wherein the anti-PD-1 antibody further comprises a humanized IgG1 or IgG4 heavy chain framework region.

11. The method of claim 7, wherein the anti-PD-1 antibody competes with Nivolumab for binding to human PD-1.

12. The method of claim 7, wherein the anti-PD-1 antibody induces IL-2 release in Mixed Lymphocyte Reaction (MLR).

* * * * *